United States Patent
Hutt Pollard et al.

(10) Patent No.: US 11,053,637 B2
(45) Date of Patent: *Jul. 6, 2021

(54) SYSTEMS AND PROCESSES FOR TREATING TEXTILES WITH AN ANTIMICROBIAL AGENT

(71) Applicant: Applied Silver, Inc., Hayward, CA (US)

(72) Inventors: Elizabeth Ann Hutt Pollard, San Francisco, CA (US); Sean Morham, San Francisco, CA (US); David E. Brown, Danville, CA (US)

(73) Assignee: APPLIED SILVER, INC., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/932,192

(22) Filed: Jul. 17, 2020

(65) Prior Publication Data

US 2020/0347543 A1 Nov. 5, 2020

Related U.S. Application Data

(63) Continuation of application No. 15/908,314, filed on Feb. 28, 2018, now Pat. No. 10,760,207.
(Continued)

(51) Int. Cl.
*D06M 16/00* (2006.01)
*D06F 35/00* (2006.01)
(Continued)

(52) U.S. Cl.
CPC .............. *D06M 11/83* (2013.01); *A61L 2/18* (2013.01); *D06F 35/00* (2013.01); *D06M 16/00* (2013.01);
(Continued)

(58) Field of Classification Search
CPC ....... D06M 11/83; D06M 16/00; D06F 35/00; D06F 39/08
See application file for complete search history.

(56) References Cited

U.S. PATENT DOCUMENTS 3,751,885 A    8/1973  McNeely
3,841,116 A   10/1974  Klein et al.
(Continued)

FOREIGN PATENT DOCUMENTS

CH     698955     12/2009
CN    1218009      6/1999
(Continued)

OTHER PUBLICATIONS

Filter Water Direct, "Hard Water can easily be treated before it damages fixtures and appliances in your home." Wayback Machine capture from Jan. 26, 2010.
(Continued)

*Primary Examiner* — Albert K Wong
(74) *Attorney, Agent, or Firm* — McDonnell Boehnen Hulbert & Berghoff LLP

(57) ABSTRACT

According to an aspect of the present disclosure, a method of treating a textile with an antimicrobial agent includes receiving a textile in a washer system. The textile includes an identification tag, which uniquely identifies the textile among a plurality of textiles. The method also includes detecting, in the washer system, the identification tag. The method further includes determining, based on the detected identification tag, one or more parameters for treating the textile with an antimicrobial agent. The antimicrobial agent includes a metallic ion. The method also includes washing the textile with a detergent, and, after washing the textile with the detergent, treating the textile with the antimicrobial agent based on the one or more parameters.

20 Claims, 10 Drawing Sheets

Related U.S. Application Data

(60) Provisional application No. 62/465,571, filed on Mar. 1, 2017.

(51) Int. Cl.
  *D06F 34/18* (2020.01)
  *D06M 11/83* (2006.01)
  *A61L 2/18* (2006.01)

(52) U.S. Cl.
  CPC ......... *D06F 34/18* (2020.02); *D06M 2200/00* (2013.01); *D10B 2401/13* (2013.01); *D10B 2501/04* (2013.01)

(56) References Cited

U.S. PATENT DOCUMENTS

| | | | |
|---|---|---|---|
| 4,048,032 A | 9/1977 | Eibl | |
| 4,098,660 A | 7/1978 | Eibl et al. | |
| 4,119,518 A | 10/1978 | Miller | |
| 4,145,291 A | 3/1979 | Console et al. | |
| 4,198,296 A | 4/1980 | Doumas et al. | |
| 4,525,253 A | 6/1985 | Hayes et al. | |
| 4,545,956 A | 10/1985 | Ciszewski et al. | |
| 4,696,742 A | 9/1987 | Shimazaki | |
| 4,710,282 A | 12/1987 | Chak et al. | |
| 4,755,268 A | 7/1988 | Matsuo et al. | |
| 4,933,870 A | 6/1990 | Chang | |
| 4,995,975 A | 2/1991 | Jacquot et al. | |
| 5,190,659 A | 3/1993 | Wang et al. | |
| 5,281,312 A | 1/1994 | Woodside | |
| 5,342,528 A | 8/1994 | Adachi et al. | |
| 5,364,512 A | 11/1994 | Earl | |
| 5,445,023 A | 8/1995 | Reed | |
| 5,632,904 A | 5/1997 | Samad et al. | |
| 5,765,403 A | 6/1998 | Lincoln et al. | |
| 5,782,109 A | 7/1998 | Spriggs et al. | |
| 5,787,537 A | 8/1998 | Mannillo | |
| 5,843,284 A | 12/1998 | Waters et al. | |
| 5,858,246 A | 1/1999 | Rafter et al. | |
| 6,022,459 A | 2/2000 | Briggs et al. | |
| 6,128,931 A | 10/2000 | Woods | |
| 6,254,894 B1 | 7/2001 | Denkewicz, Jr. et al. | |
| 6,267,885 B1 | 7/2001 | Briggs et al. | |
| 6,303,039 B1 | 10/2001 | Back et al. | |
| 6,398,927 B1 | 6/2002 | Merzhauser | |
| 6,508,929 B1 | 1/2003 | Mercer | |
| 6,514,406 B1 | 2/2003 | Katehis | |
| 6,524,540 B1 | 2/2003 | Heinig, Jr. | |
| 6,562,243 B2 | 5/2003 | Sherman | |
| 6,634,048 B1 | 10/2003 | Hornung et al. | |
| 6,641,829 B1 | 11/2003 | Green et al. | |
| 6,761,827 B2 | 7/2004 | Coffey | |
| 6,838,095 B2 | 1/2005 | Newman et al. | |
| 6,929,740 B2 | 8/2005 | Hayes | |
| 6,982,039 B1 | 1/2006 | Butkus et al. | |
| 7,012,053 B1 | 3/2006 | Bamabus et al. | |
| 7,152,759 B2 | 12/2006 | Walton | |
| 7,322,065 B2 | 1/2008 | Kim et al. | |
| 7,384,564 B2 | 6/2008 | Bo | |
| 7,413,667 B1 | 8/2008 | Routberg et al. | |
| 7,422,759 B2 | 9/2008 | Kepner et al. | |
| 7,481,081 B2 | 1/2009 | Hsu et al. | |
| 7,487,876 B2 | 2/2009 | Maeda | |
| 7,540,966 B2 | 6/2009 | Costa et al. | |
| 7,597,718 B2 | 10/2009 | Yoshikawa et al. | |
| 7,617,704 B2 | 11/2009 | Iimori et al. | |
| 7,624,601 B2 | 12/2009 | Ikemizu et al. | |
| 7,708,896 B2 | 5/2010 | Ooe et al. | |
| 7,807,199 B2 | 10/2010 | Allen et al. | |
| 7,807,661 B2 | 10/2010 | Ylitalo et al. | |
| 7,819,127 B1 | 10/2010 | Huffman | |
| 7,882,647 B2 | 2/2011 | Ikemizu | |
| 7,934,402 B2 | 5/2011 | Lee | |
| 7,942,024 B2 | 5/2011 | Lee | |
| 7,950,254 B2 | 5/2011 | Gray et al. | |
| 7,972,519 B2 | 7/2011 | Koos et al. | |
| 8,002,898 B2 | 8/2011 | Schepers et al. | |
| 8,118,912 B2 | 2/2012 | Rodriguez et al. | |
| 8,173,067 B2 | 5/2012 | Eldred | |
| 8,239,990 B2 | 8/2012 | Lim et al. | |
| 8,309,506 B2 | 11/2012 | Sunder et al. | |
| 8,361,505 B1 | 1/2013 | Perry | |
| 8,394,420 B2 | 3/2013 | Kepner et al. | |
| 8,449,732 B2 | 5/2013 | Choi | |
| 8,460,395 B2 | 6/2013 | Smulowitz | |
| 8,563,447 B2 | 10/2013 | Canada | |
| 8,641,947 B2 | 2/2014 | Schmuhl et al. | |
| 8,729,008 B2 | 5/2014 | Begli et al. | |
| 9,132,296 B2 | 9/2015 | Wingfield | |
| 2001/0049846 A1 | 12/2001 | Guzzi et al. | |
| 2002/0189954 A1 | 12/2002 | Miyazaki et al. | |
| 2003/0170453 A1 | 9/2003 | Foss et al. | |
| 2003/0190370 A1 | 10/2003 | Kim et al. | |
| 2003/0196282 A1 | 10/2003 | Fyvie et al. | |
| 2003/0230122 A1 | 12/2003 | Lee | |
| 2004/0025263 A1 | 2/2004 | Kim et al. | |
| 2004/0031764 A1 | 2/2004 | Heinig, Jr. | |
| 2004/0205899 A1 | 10/2004 | Park et al. | |
| 2004/0214495 A1 | 10/2004 | Foss et al. | |
| 2005/0019568 A1 | 1/2005 | Foss et al. | |
| 2005/0037057 A1 | 2/2005 | Schuette et al. | |
| 2005/0095158 A1 | 5/2005 | Kirschner et al. | |
| 2005/0118281 A1 | 6/2005 | Newman et al. | |
| 2005/0155939 A1 | 7/2005 | Stadelmann | |
| 2005/0188731 A1 | 9/2005 | Aouad | |
| 2005/0194297 A1 | 9/2005 | Dorward | |
| 2005/0224419 A1 | 10/2005 | Wien et al. | |
| 2005/0226914 A1 | 10/2005 | Cottrell et al. | |
| 2005/0229327 A1 | 10/2005 | Casella et al. | |
| 2005/0252255 A1 | 11/2005 | Gray et al. | |
| 2006/0110258 A1 | 5/2006 | Iimura et al. | |
| 2006/0123562 A1 | 6/2006 | Ghosh et al. | |
| 2006/0127457 A1 | 6/2006 | Buchalter | |
| 2006/0130533 A1 | 6/2006 | Ooe et al. | |
| 2006/0163135 A1 | 7/2006 | Ellis et al. | |
| 2006/0164093 A1 | 7/2006 | Ooe | |
| 2006/0186222 A1 | 8/2006 | Ikemizu et al. | |
| 2006/0265814 A1 | 11/2006 | Ritter | |
| 2007/0004300 A1 | 1/2007 | Kreider et al. | |
| 2007/0044820 A1 | 3/2007 | Chan et al. | |
| 2007/0045176 A1 | 3/2007 | Chandra et al. | |
| 2007/0134301 A1 | 6/2007 | Ylitalo et al. | |
| 2007/0163097 A1 | 7/2007 | Metcalfe et al. | |
| 2007/0175833 A1 | 8/2007 | Ikeboh et al. | |
| 2007/0243380 A1 | 10/2007 | Vegad et al. | |
| 2007/0243781 A1 | 10/2007 | Chou | |
| 2007/0251022 A1 | 11/2007 | Yoshikawa et al. | |
| 2008/0016919 A1 | 1/2008 | Lee | |
| 2008/0023385 A1 | 1/2008 | Baker, Jr. et al. | |
| 2008/0041117 A1 | 2/2008 | Lee | |
| 2008/0085326 A1 | 4/2008 | Ruan | |
| 2008/0131471 A1 | 6/2008 | Kolbe et al. | |
| 2008/0136648 A1* | 6/2008 | Endrikhovski | G06F 11/1456 340/572.8 |
| 2008/0217807 A1 | 9/2008 | Lee et al. | |
| 2008/0248075 A1 | 10/2008 | Brambilla et al. | |
| 2008/0256719 A1 | 10/2008 | Radev | |
| 2008/0267812 A1 | 10/2008 | Kawachi et al. | |
| 2008/0299006 A1 | 12/2008 | Ikemizu | |
| 2008/0302713 A1 | 12/2008 | Patrick | |
| 2009/0000040 A1 | 1/2009 | Ikemizu | |
| 2009/0104239 A1 | 4/2009 | Parsons et al. | |
| 2009/0181592 A1 | 7/2009 | Dugan | |
| 2009/0193593 A1 | 8/2009 | Kirigakubo et al. | |
| 2009/0218266 A1 | 9/2009 | Sawafta et al. | |
| 2009/0259157 A1 | 10/2009 | Thomas | |
| 2010/0000268 A1 | 1/2010 | Kohne | |
| 2010/0047321 A1 | 2/2010 | Sandford et al. | |
| 2010/0050872 A1 | 3/2010 | Lee | |
| 2010/0102002 A1 | 4/2010 | O'Brien et al. | |
| 2010/0116689 A1 | 5/2010 | Greene et al. | |
| 2010/0140185 A1 | 6/2010 | Hill | |
| 2010/0183739 A1 | 7/2010 | Newman | |
| 2010/0193449 A1 | 8/2010 | Shang et al. | |

(56) References Cited

U.S. PATENT DOCUMENTS

| | | |
|---|---|---|
| 2010/0243432 A1 | 9/2010 | Ikemizu |
| 2011/0017609 A1 | 1/2011 | Choi |
| 2011/0094972 A1 | 4/2011 | King et al. |
| 2011/0100838 A1 | 5/2011 | Kim et al. |
| 2011/0120921 A1 | 5/2011 | Kim |
| 2011/0139632 A1 | 6/2011 | Beringer et al. |
| 2011/0180423 A1 | 7/2011 | Barry et al. |
| 2011/0224120 A1 | 9/2011 | Meine et al. |
| 2011/0225741 A1 | 9/2011 | Poy et al. |
| 2011/0262556 A1 | 10/2011 | Holladay et al. |
| 2011/0297609 A1 | 12/2011 | Hu |
| 2012/0003326 A1 | 1/2012 | Meine et al. |
| 2012/0055862 A1 | 3/2012 | Parekh et al. |
| 2012/0091070 A1 | 4/2012 | Sjaunta et al. |
| 2012/0187052 A1 | 7/2012 | Elliott |
| 2012/0192363 A1 | 8/2012 | King |
| 2012/0213665 A1 | 8/2012 | Bik et al. |
| 2013/0022686 A1 | 1/2013 | Rademan et al. |
| 2013/0281345 A1 | 10/2013 | Burkinshaw et al. |
| 2013/0327419 A1 | 12/2013 | Morham |
| 2014/0157526 A1* | 6/2014 | Larmo .............. D06F 33/00 8/137 |
| 2014/0202943 A1 | 7/2014 | Pradeep et al. |
| 2014/0259441 A1* | 9/2014 | Fulmer .............. D06F 33/00 8/137 |
| 2014/0304925 A1* | 10/2014 | Bringewatt .......... D06F 31/005 8/137 |
| 2014/0369953 A1 | 12/2014 | Purschwitz et al. |
| 2015/0047718 A1 | 2/2015 | Brown et al. |
| 2015/0159314 A1 | 6/2015 | Morham et al. |
| 2015/0159319 A1 | 6/2015 | Morris et al. |
| 2017/0008783 A1 | 1/2017 | Brown et al. |
| 2017/0050870 A1* | 2/2017 | Brezoczky .......... D06F 35/008 |

FOREIGN PATENT DOCUMENTS

| | | |
|---|---|---|
| CN | 1558016 | 12/2004 |
| CN | 1671911 | 9/2005 |
| CN | 2725278 | 9/2005 |
| CN | 2753774 | 1/2006 |
| CN | 2780804 | 5/2006 |
| CN | 200984347 | 12/2007 |
| CN | 101411958 | 4/2008 |
| CN | 201056507 | 5/2008 |
| CN | 101307555 | 11/2008 |
| CN | 201254480 | 6/2009 |
| CN | 101670123 | 3/2010 |
| CN | 101731269 | 6/2010 |
| CN | 101863581 | 10/2010 |
| CN | 101864670 | 10/2010 |
| CN | 101926363 | 12/2010 |
| CN | 101967025 | 2/2011 |
| CN | 201737797 | 2/2011 |
| CN | 201738163 | 2/2011 |
| CN | 101991870 | 3/2011 |
| CN | 21791121 | 4/2011 |
| CN | 201791121 | 4/2011 |
| CN | 201873556 | 6/2011 |
| CN | 201902711 | 7/2011 |
| CN | 202021117 | 11/2011 |
| CN | 202023990 | 11/2011 |
| CN | 202036069 | 11/2011 |
| CN | 102330844 | 1/2012 |
| CN | 202121806 | 1/2012 |
| CN | 102421295 | 4/2012 |
| CN | 102535114 | 7/2012 |
| CN | 202386643 | 8/2012 |
| CN | 202390678 | 8/2012 |
| CN | 102666397 | 9/2012 |
| CN | 202410344 | 9/2012 |
| CN | 202430491 | 9/2012 |
| CN | 102781814 | 11/2012 |
| DE | 19853193 | 5/2000 |
| DE | 102007034215 | 5/2008 |
| EP | 128782 | 11/1987 |
| EP | 1296895 | 4/2003 |
| EP | 1334073 | 8/2003 |
| EP | 1600545 | 11/2005 |
| EP | 1785518 | 5/2007 |
| EP | 1983085 | 10/2008 |
| EP | 2045389 | 4/2009 |
| EP | 2302122 A1 | 3/2011 |
| EP | 2461676 | 6/2012 |
| EP | 2499916 | 9/2012 |
| EP | 2513370 | 10/2012 |
| EP | 2544804 | 1/2013 |
| EP | 2674523 | 12/2013 |
| GB | 2298858 | 3/1995 |
| GB | 2419590 | 5/2006 |
| JP | H0560721 | 3/1993 |
| JP | 2001025772 | 1/2001 |
| JP | 2001062458 | 3/2001 |
| JP | 2001066090 | 3/2001 |
| JP | 2001276484 | 10/2001 |
| JP | 2001340281 | 12/2001 |
| JP | 2002113288 | 4/2002 |
| JP | 2004057423 | 4/2004 |
| JP | 2004105692 | 4/2004 |
| JP | 2004313752 | 11/2004 |
| JP | 2004346024 | 12/2004 |
| JP | 2005098606 | 4/2005 |
| JP | 2005261830 | 9/2005 |
| JP | 2005296671 | 10/2005 |
| JP | 2007061757 | 3/2007 |
| JP | 2008119287 | 5/2008 |
| JP | 2007167785 | 7/2008 |
| JP | 2008183283 | 8/2008 |
| JP | 2008220450 | 9/2008 |
| JP | 2008279056 | 11/2008 |
| JP | 2009017907 | 1/2009 |
| JP | 2009039320 | 2/2009 |
| JP | 2010136738 | 6/2010 |
| JP | 2010136739 | 6/2010 |
| JP | 2010194484 | 9/2010 |
| JP | 2012161728 | 8/2012 |
| JP | 2014176448 | 9/2014 |
| KR | 1990069099 | 9/1999 |
| KR | 20000037120 | 7/2000 |
| KR | 20020012369 | 2/2002 |
| KR | 20050012369 | 2/2002 |
| KR | 20020074306 | 9/2002 |
| KR | 20040085107 | 10/2004 |
| KR | 20040093957 | 11/2004 |
| KR | 20050004614 | 1/2005 |
| KR | 20050004616 | 1/2005 |
| KR | 20050004618 | 1/2005 |
| KR | 20050004620 | 1/2005 |
| KR | 20050004621 | 1/2005 |
| KR | 20050004623 | 1/2005 |
| KR | 20050004625 | 1/2005 |
| KR | 20050004626 | 1/2005 |
| KR | 20050065718 | 6/2005 |
| KR | 20050068357 | 7/2005 |
| KR | 20050089257 | 9/2005 |
| KR | 20070028012 | 3/2007 |
| KR | 100736819 | 7/2007 |
| KR | 100818561 | 4/2008 |
| KR | 20080075694 | 8/2008 |
| KR | 20090001293 | 1/2009 |
| KR | 20090090501 | 8/2009 |
| KR | 20110062719 | 6/2011 |
| KR | 20110075870 | 7/2011 |
| KR | 20120000652 | 1/2012 |
| KR | 101430906 | 8/2014 |
| MD | 2940 | 12/2005 |
| RU | 2135417 | 8/1999 |
| RU | 2182128 | 5/2002 |
| RU | 2193528 | 11/2002 |
| RU | 2264990 | 11/2005 |
| RU | 2324026 | 5/2008 |
| RU | 2373156 | 11/2009 |
| RU | 2381182 | 2/2010 |
| TW | 252268 | 4/2006 |

(56) References Cited

FOREIGN PATENT DOCUMENTS

| | | |
|---|---|---|
| TW | 200902790 | 1/2009 |
| TW | 201013008 | 4/2010 |
| TW | 201127948 | 8/2011 |
| TW | 201138638 | 11/2011 |
| UA | 22673 | 4/2007 |
| WO | WO 1999039749 | 8/1999 |
| WO | WO 2002036499 | 5/2002 |
| WO | WO 2003051780 | 5/2003 |
| WO | WO 2004104153 | 12/2004 |
| WO | WO 2006014080 | 1/2006 |
| WO | WO 2006129982 | 12/2006 |
| WO | WO 2007057077 | 5/2007 |
| WO | WO 2008075992 | 6/2008 |
| WO | WO 2011015429 | 2/2011 |
| WO | WO 2011067748 | 6/2011 |
| WO | WO 2011073697 | 6/2011 |
| WO | WO 2011110550 | 9/2011 |
| WO | WO 2011126395 | 10/2011 |
| WO | WO 2011139835 | 11/2011 |
| WO | WO 2012025943 | 3/2012 |
| WO | WO 2012031853 | 3/2012 |
| WO | WO 2012059992 | 5/2012 |
| WO | WO 2012077122 | 6/2012 |
| WO | WO 2012095665 | 7/2012 |
| WO | WO 2012095828 | 7/2012 |
| WO | WO 2012107422 | 8/2012 |
| WO | WO 2012140520 | 10/2012 |
| WO | WO 2012142025 | 10/2012 |
| WO | WO 2012150506 | 11/2012 |
| WO | WO 2012155269 | 11/2012 |
| WO | WO 2014196881 | 12/2014 |
| WO | WO 2015001870 | 1/2015 |
| WO | WO 2015084568 | 6/2015 |
| WO | WO 2015084569 | 6/2015 |
| WO | WO 2017034884 | 3/2017 |
| WO | WO 2017197260 | 11/2017 |

OTHER PUBLICATIONS

International Search Report issued in International Application No. PCT/US18/20245; ISA/US, dated May 10, 2018, 2 ages.
Liu et al., "Controlled Release of Biologically Active Silver from Nanosilver Surfaces," ACS Nano, 2010, pp. 903-6913, vol. 4, No. 11.
Mitrano et al., "Presence of Nanoparticles in Wash Water from Conventional Silver and Nano-silver Textiles," ACS Nano, 2014, pp. 7208-7219, vol. 8, No. 7.
Putro et al., "Silver Nano Perfume Ejector to Destroy Bacteria for Clothes," AASIC, 2013, pp. 72-75.
Written Opinion issued in International Application No. PCT/US18/20245; ISA/US, dated May 10, 2018, 7 pages.
European Search Report Issued in European Application No. 18761722.0, dated Feb. 9, 2021, 10 pages.
"Smart Machine for Segregation and Sanitation of Garments," ED—Darl Kuhn, IP.Com, IP.Com Inc., West Henrietta, NY, US, Jan. 22, 2010.

* cited by examiner

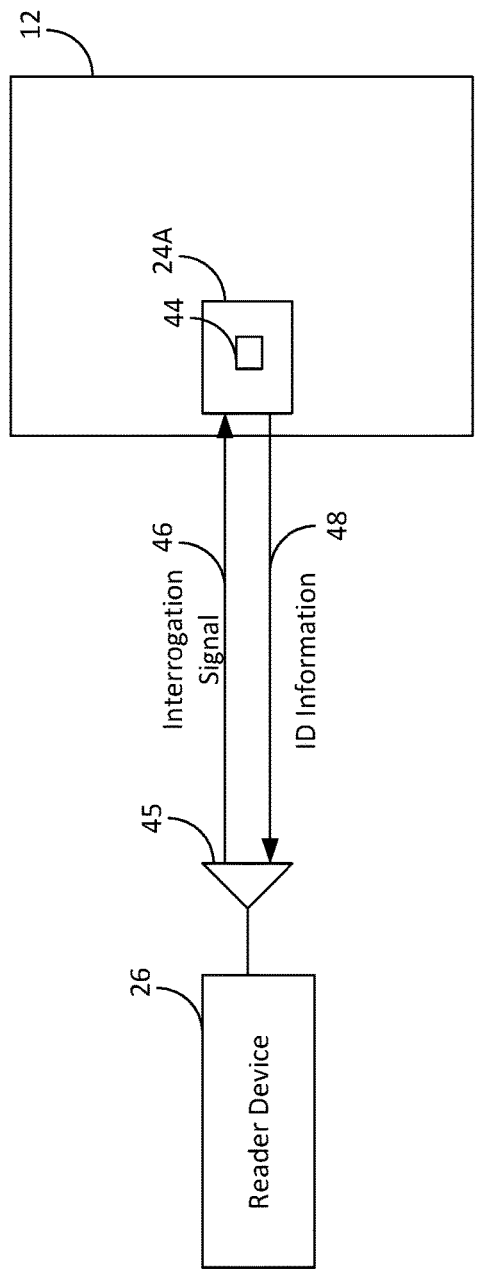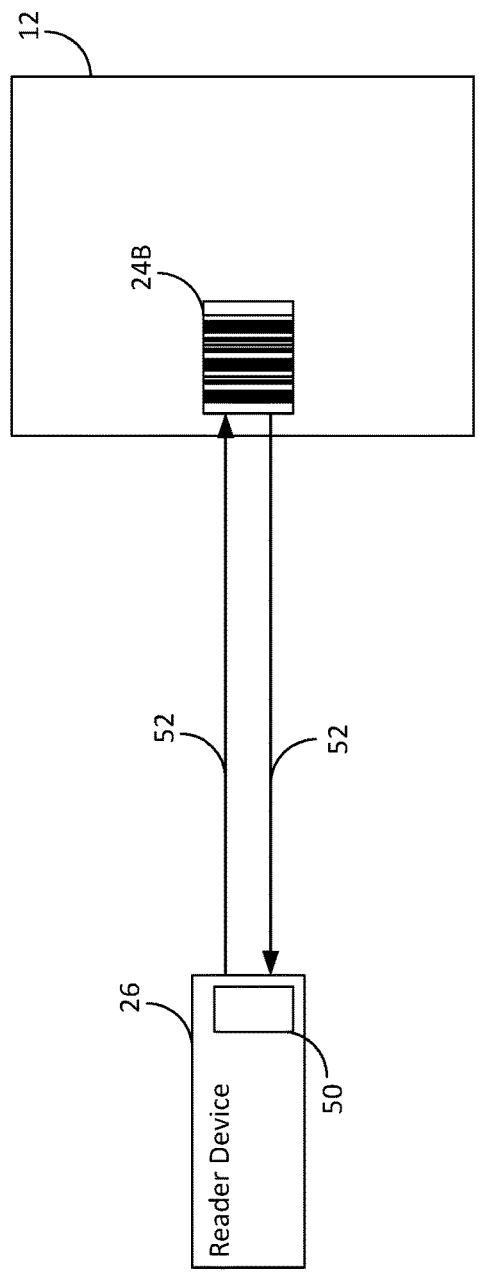

SYSTEMS AND PROCESSES FOR TREATING TEXTILES WITH AN ANTIMICROBIAL AGENT

CROSS-REFERENCE TO RELATED APPLICATION

This application is a continuation of U.S. patent application Ser. No. 15/908,314, filed on Feb. 28, 2018, which claims the benefit of U.S. Provisional Application No. 62/465,571, filed Mar. 1, 2017, which are hereby incorporated by reference in their entirety.

FIELD

The disclosure is directed to systems and methods for treating textiles with an antimicrobial agent.

BACKGROUND

Microbial contamination of textiles can contribute to the spread of infectious diseases, including healthcare associated infections, which are among the leading causes of preventable deaths in the United States and are associated with a substantial increase in health care costs each year. In other instances, microbial contaminations can cause unsightly stains and unpleasant odors.

Textiles having antimicrobial properties can help reduce (or eliminate) microbial contaminations of textiles. In one prior approach to providing a textile having antimicrobial properties, the textile is treated with an antimicrobial agent during a textile manufacturing process. For example, the fibers of the textile are embedded or coated with antimicrobial agent during the manufacturing process. However, the total amount of antimicrobial agent is fixed at the point of conversion of the fibers into a textile and the efficacy declines over time as the antimicrobial agent in the fabric is washed away when laundered and never restored. Moreover, this approach has proven to be unsatisfactory to market participants.

In addition to the efficacy/performance issues noted above, these products require commercial linen users, such as hospitals and other health care delivery facilities, to make a large upfront capital investment to purchase a new, antimicrobial agent-impregnated, linen inventory and discard existing and otherwise useable inventory. Further, the products may exhibit a soiled off-white discoloration appearance, may be uncomfortable to the touch, and are known to be difficult to launder, dry and press verses traditional linens.

SUMMARY

In one aspect, the disclosure is directed to a method of treating a textile with an antimicrobial agent includes receiving a textile in a washer system. The textile includes an identification tag, which uniquely identifies the textile among a plurality of textiles. The method also includes detecting, in the washer system, the identification tag. The method further includes determining, based on the detected identification tag, one or more parameters for treating the textile with an antimicrobial agent. The antimicrobial agent includes a metallic ion. The method also includes washing the textile with a detergent, and, after washing the textile with the detergent, treating the textile with the antimicrobial agent based on the one or more parameters.

BRIEF DESCRIPTION OF THE DRAWINGS

FIG. 2 is a simplified block diagram of a reader device and textile according to an example embodiment.

FIG. 3 is a simplified block diagram of a reader device and textile according to an example embodiment.

Figure 1:
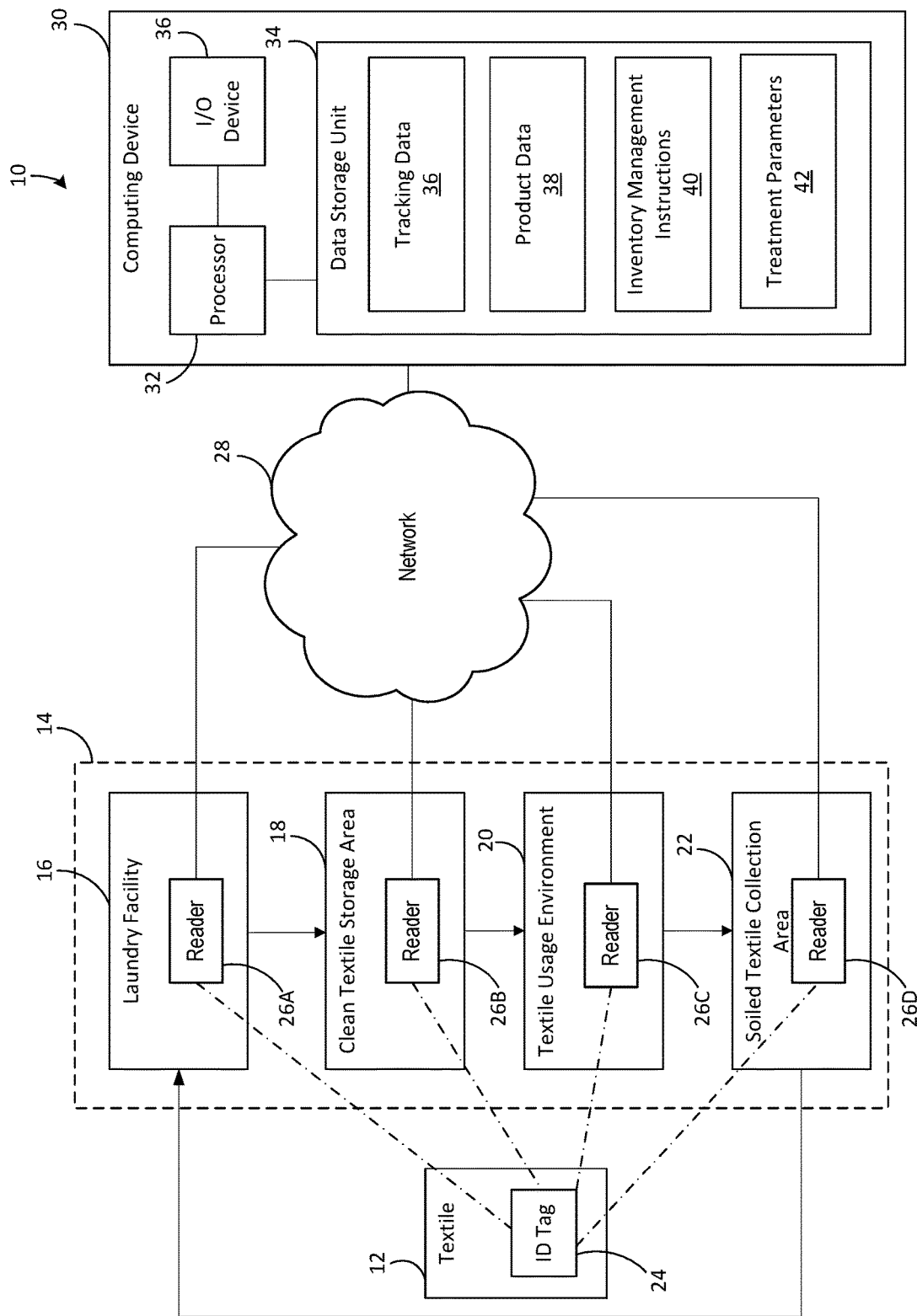
FIG. 1 is a simplified block diagram of a system in which a textile may be used according to an example embodiment.

While the invention is susceptible to various modifications and alternative forms, specific embodiments have been shown by way of example in the Figures and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims. It should be understood that other embodiments may include more or less of each element shown in a given Figure. Further, some of the illustrated elements may be combined or omitted. Yet further, an example embodiment may include elements that are not illustrated in the Figures.

DESCRIPTION

The following description describes various features and functions of the disclosed systems and methods with reference to the accompanying figures. In the Figures, similar symbols typically identify similar components, unless context dictates otherwise. The illustrative systems and methods described herein are not meant to be limiting. It will be readily understood that certain aspects of the disclosed systems and methods can be arranged and combined in a wide variety of different configurations, all of which are contemplated herein.

According to aspects of the disclosure, systems and processes are described and illustrated for treating a textile with an antimicrobial agent. The terms fabric, linen, and textile are used interchangeably herein. Aspects of the disclosure may be described in the context of a single textile for ease of description; however, it should be understood that such aspects can be extended to include processes and systems in the context of multiple textiles such as an inventory of textiles having multiple pieces.

Within examples, the textile is treated with the antimicrobial agent during one or more laundry cycles in a washer system. At any given time, the amount of antimicrobial agent contained in the textile is based on various factors such as, for example, a number of laundry cycles the textile has undergone, a concentration of the antimicrobial agent in a treatment solution of each laundry cycle, and/or an amount of time the textile is exposed to the treatment solution for each laundry cycle. After one or more of the laundry cycles, the textile may achieve a level of efficacy that can reduce or eliminate microbial contamination of the textile.

Given that the amount of antimicrobial agent in a textile is based on various factors, which may change from one laundry cycle to the next for a particular textile, using the same parameters for each laundry cycle of the textile may lead to inefficiencies. For example, if the same concentration of the antimicrobial agent is used to treat the textile for each laundry cycle, the washer system may unnecessarily use excessive amounts of antimicrobial agent for later laundry cycles performed after the textile achieves efficacy (i.e., as a result of an earlier laundry cycle).

The systems and methods of the present disclosure can reduce (or eliminate) such inefficiencies by configuring one or more parameters for performing a laundry cycle to treat a textile based, at least in part, on tracking data associated with the textile. The tracking data associated with the textile can be determined based on one or more reader devices detecting an identification tag coupled to the textile as the textile moves through one or more locations of the system. As an example, the reader device(s) can include a radio frequency identification (RFID) interrogator that scans an RFID tag of the textile. As another example, the reader device(s) can include a barcode scanner and the identification tag can include a barcode. More generally, the identification tag provides identification information that uniquely identifies the textile among a plurality of textiles that may be laundered and/or used in the system, and the reader device can detect the identification tag so as to determine the identification information from the identification tag.

As examples, the tracking data associated with the textile can include data representing (i) a number of times the textile was washed with a detergent, (ii) a number of times the textile was treated with the antimicrobial agent, (iii) a concentration of a treatment solution applied to the textile during one or more laundry cycles, (iv) an amount of time that the textile was washed and/or treated during the laundry cycle(s), (v) an amount of time that the textile was agitated during the laundry cycle(s), (vi) a rate of addition of the antimicrobial agent (i.e., a dosing rate) to form the treatment solution for treating the textile with the antimicrobial agent during the laundry cycle(s), and/or (vii) a quality of the water that was used to wash and/or treat the textile during the laundry cycle(s). The system can determine additional or alternative types of tracking data in other examples.

Within examples, the reader devices can be positioned at one or more locations within a washer system to facilitate determining the tracking data for each laundry cycle of the textile. For instance, a reader device can be positioned at an intake to the washer system to detect and record each time the textile enters the washer system. In additional or alternative examples, the system can include reader device(s) at one or more additional zones and/or modules within a washer system to facilitate tracking the progress of the textile through the washer system (e.g., in a wash zone, a neutralization zone, a treatment zone, etc.).

In additional or alternative examples, the one or more reader devices can be located at a plurality of locations within a broader system (e.g., a healthcare system, a hospital system, a hotel system, etc.). For example, the reader device(s) can be located in a laundry facility, a clean textile storage area, a textile usage environment, a soiled textile collection area, and/or transport devices. By detecting the identification tag of the textile at these locations, the system can track the textile at different points in the usage cycle of the textile. This can facilitate the system providing an inventory tracking system that can be used to achieve efficient handling of textile order fulfillment, maintaining appropriate stock levels of textiles, maintaining and ordering stock of the antimicrobial agent, and/or maintaining and ordering stock of detergent.

In one example, the system can utilize the tracking data to determine an expected amount of antimicrobial agent that is needed to maintain a predetermined level of efficacy within an inventory of textiles for a given period of time. The system can additionally or alternatively determine whether a stock of antimicrobial agent currently available to the system is sufficient to meet the expected demand for the antimicrobial agent over that period of time and, if the system determines that the stock is not sufficient, the system can cause additional stock of the antimicrobial agent to be ordered. In this way, the system can use the tracking data to perform predictive analytics, which improve efficiency of the system. Additionally, such predictive analytics can facilitate reducing the storage space required to store the stock of antimicrobial agent and/or reducing down time of the system due to the system awaiting the delivery of additional stock of antimicrobial agent. In an additional or alternative example, the system can perform a similar process with respect to the stock of detergent available to the system.

In additional or alternative examples, the system can also configure the parameter(s) for treating the textile based on product data associated with the textile. For example, the product data can include data representing (i) a type of textile (e.g., a gown, a bedsheet, a blanket, clothing, a pillow case, etc.), (ii) a material of the textile, and/or (iii) a manufacture date of the textile (i.e., an age of the textile). Some types of textiles may be used by end-users in contexts that may benefit from a different an amount of antimicrobial agent in the textiles as compared to other types of textiles that are used in other contexts. For example, a textile that is expected to come into contact with bodily fluids may benefit from having a greater amount of antimicrobial agent than a textile that is not expected to come into contact with bodily fluids. In general, the system can store the product data in association with the unique identification information corresponding to the textile.

In one example, the system can further use the tracking data and/or the product data to determine when the textile has reached the end of its useful life and remove the textile from the system for disposal and/or recycling. For instance, the system can use the tracking data to determine when the textile has been washed and/or treated greater than a threshold number of times and, based on such determination, remove the textile from the system. This may help to avoid discoloration of textiles due to excessive exposure to the antimicrobial agent.

In additional or alternative examples, the tracking data can include patient- and/or medical-related information. For instance, when a textile is provided to a patient, the reader device can scan the identification tag on the textile and a patient-identification tag (e.g., a barcode and/or RFID tag on a patient identification bracelet). Based on these initial scans, the reader device can signal to the system that the patient began using the textile and the system can record tracking data including a first timestamp. After the patient uses the textile, the textile is retrieved from the patient and the reader device can again scan the identification tag on the textile and the patient-identification tag. Based on these subsequent scans, the reader device can signal the system that the patient stopped using the textile and the system can record tracking data including a second timestamp. Thus, by scanning the identification tag of the textile and the patient-identification tag when the textile is provided to and retrieved from the patient, the system can obtain tracking data indicating the time period during which the patient used the textile.

In one implementation, the system can access a medical record associated with the patient (e.g., based on information from the scanned patient-identification tag) to determine information relating to medical procedures performed on the patient and/or health conditions of the patient for the time period during which the patient used the textile. The system can incorporate this medical procedure information and/or health condition information in the tracking data stored for the textile. In this way, the system can configure the parameter(s) for treating the textile based on the medical procedure and/or the patient health condition that encountered by the textile during use.

Additionally, for example, by tracking which patients used a textile and the times of such use, the system can provide information that can help to address healthcare acquired infections in a healthcare system. For instance, if it is determined that a contamination occurred in a specific location of the healthcare system (e.g., a specific operating room), the system can use the stored tracking data to determine information indicating which textiles passed through the location, at what times the textiles passed through the location, and which patients were using the textiles at that time. Personnel can then use this information to investigate the source of the contamination, and/or identify patients that should be checked for potential health problems due to the contamination. The tracking information can also be used to determine other locations that the identified textiles passed through after passing through the contaminated location to determine whether the contamination spread to additional locations in the healthcare system that have not yet been identified as having a contamination.

Similarly, if a patient is determined to have a health condition caused by a contamination, the system can use the tracking data to determine the textile(s) that the patient used and the times of such use. Personnel can then determine which other patients used those textiles after the identified times so that the personnel can check the identified patients for potential health problems. Additionally, in some implementations, the system can flag the identified textile as requiring more extensive antimicrobial agent treatment and/or cause the textiles to be removed from the system. In these ways, the system can facilitate reducing healthcare acquired infections within the healthcare system.

Referring now to FIG. 1, a simplified block diagram of a system 10 for treating textiles 12 with an antimicrobial agent based on tracking information is illustrated according to an example. As shown in FIG. 1, the system 10 includes a plurality of areas 14 through which the textiles 12 may pass while in use. For example, in FIG. 1, the areas 14 include a laundry facility 16, a clean textile storage area 18, a textile usage environment 20, and a soiled collection area 22 in FIG. 1. The laundry facility 14 can carry out a laundry process to wash the textiles 12 and/or treat the textiles 12 with an antimicrobial agent. Example washer systems for carrying out laundry processes are described below.

After each textile 12 is cleaned, the textile 12 can be transferred from the laundry facility 16 to the clean textile storage area 18. The clean textile storage area 18 can store the textiles 12 until needed for use and, thus, can provide one or more centralized locations for maintaining a portion of an inventory of textiles that is ready for deployment. For example, the clean textile storage area 18 can include a plurality of shelves and/or storage containers for storing the textiles 12 according to various criteria such as, for example, type and/or size.

When needed for use, the textiles 12 are transferred to the textile usage environment 20. As examples, the textile usage environment 20 can be a healthcare facility, a hospital, a hotel, and/or an athletic facility. For instance, the textiles 12 can be used by doctors, nurses, hospital personnel, and/or patients in the textile usage environment 20. As a result of such usage, the textiles 12 may become soiled. Once soiled, the textiles 12 are transferred to the soiled textile collection area 22. For example, the soiled textile collection area 22 can include a laundry shoot and/or linen hampers, which facilitate collecting the soiled textiles 12 in one or more centralized locations.

The textiles 12 can then be transferred from the soiled textile collection area 22 to the laundry facility 14 to repeat the process. Within examples, the laundry facility 14 can be located locally and/or remotely from the clean textile storage area 18, the textile usage environment 20, and/or the soiled collection area 22. Although the areas 14 of the system 10 includes the laundry facility 16, the clean textile storage area 18, the textile usage environment 20, and the soiled collection area 22 in FIG. 1, the system 10 can include additional or alternative areas 14 in other examples.

As also shown in FIG. 1, the textile 12 includes an identification tag 24 and the areas 14 each include a reader device 26A-26D. In FIG. 1, the laundry facility 16 includes a first reader device 26A that can detect the identification tag 24 when the textile 12 is in the laundry facility 16, the clean textile storage area 18 includes a second reader device 26B that can detect the identification tag 24 when the textile 12 is in the clean textile storage area 18, the textile usage environment 20 includes a third reader device 26C that can detect the identification tag 24 when the textile 12 is in the usage environment 20, and the soiled textile collection area 22 includes a fourth reader device 26D that can detect the identification tag 24 when the textile 12 is in the soiled collection area 22.

In one example, the reader devices 26A-26D can include a RFID interrogator and the identification tag 24 can include a RFID tag. As additional or alternative example, the reader devices 26A-26D can include a barcode scanner and the identification tag 24 can include a barcode. More generally, the identification tag 24 provides identification information that uniquely identifies the textile 12 among a plurality of textiles that may be laundered and/or used in the system 10, and the reader devices 26A-26D can detect the identification tag 24 so as to determine the identification information from the identification tag 24.

The reader devices 26A-26D are communicatively coupled (e.g., via wireless and/or wired connections over a network 28) to a computing device 30. The computing device 30 includes a processor 32, a data storage unit 34, and an input/output device 36.

The processor 32 may include a general-purpose processor (e.g., a microprocessor) and/or a special-purpose processor (e.g., a digital signal processor (DSP)). The data storage unit 34 can have one or more volatile, non-volatile, removable, and/or non-removable storage components, such as magnetic, optical, or flash storage, and/or may be integrated in whole or in part with processor 32. Further, the data storage unit 34 may take the form of a non-transitory computer-readable storage medium, having stored thereon program instructions (e.g., compiled or non-compiled program logic and/or machine code) that, when executed by processor 32, cause the system 10 to perform one or more acts and/or functions, such as those described in this disclosure. As such, system 10 may be configured to perform one or more acts and/or functions, such as those described in this disclosure. Such program instructions may define and/or be part of a discrete software application that can be executed in response to certain inputs being received from a communication interface and/or a user interface, for instance. The data storage unit 34 may also store other types of data, such as those types described in this disclosure.

In general, when the textile 12 enters, exits, and/or is present in one of the areas 14, the corresponding reader device 26A-26D in the area 14 communicates with the identification tag 24 to determine the identification information associated with the textile 12. The reader device 26A-26D transmits the determined identification information to the computing device 30. The processor 32 processes the identification information to determine and/or update tracking data 36 stored in the data storage unit 34. For instance, the computing system 30 can utilize a database that specifies for each textile, on a per textile basis, one or more records of associated data items for: (i) the unique identification information corresponding to the identification tag 24 of the textile 12 and (ii) a time and location of the identification tag 24 being detected. In this way, the tracking data 36 can provide a log indicating the current location of the textile 12 in the system 10 and/or a history of past locations of the textile 12 in the system 10.

As will be described further below, the tracking data 36 can also include data items for i) a number of times the textile 12 was washed with a detergent, (ii) a number of times the textile 12 was treated with an antimicrobial agent, (iii) a concentration of a treatment solution applied to the textile 12 during one or more laundry cycles, (iv) an amount of time that the textile 12 was washed and/or treated during the laundry cycle(s), (v) an amount of time that the textile 12 was agitated during the laundry cycle(s), (vi) a rate of addition of the antimicrobial agent to form the treatment solution for treating the textile with the antimicrobial agent during the laundry cycle(s), and/or (vii) a quality of the water that was used to wash and/or treat the textile during the laundry cycle(s).

As also shown in FIG. 1, the data storage unit 34 can store product data 38 for each textile 12. For instance, the database can further specify for each textile one or more records of associated data items for the (i) unique identification information corresponding to the identification tag 24 of the textile 12, (ii) a type of textile (e.g., a gown, a bedsheet, a blanket, clothing, a pillow case, etc.), (iii) a material of the textile, and/or (iv) a manufacture date of the textile (i.e., an age of the textile).

The data storage unit 34 can further store inventory management instructions 40, which the computing system 30 may use to control the performance of tasks and actions relating to the textile 12 at the different areas 14 of the system 10. For example, the computing system 30 can use the inventory management instructions 40 to cause the textile 12 to be moved from one area 14 to another area 14 in the system 10, and/or to order additional antimicrobial agent and/or detergent for use at the laundry facility 16.

The data storage unit 36 can also store treatment parameters 42. The computing system 30 can provide the treatment parameters 42 to a washer system at the laundry facility 16 to control operation of the washer system during a laundry cycle. For instance, the computing system 30 can determine one or more treatment parameters 42 from among a plurality of possible treatment parameters 42 for a particular laundry cycle of the textile 12 based on an analysis of the tracking data 36 and/or product data 38 stored for the textile 12. In this way, the computing system 30 can dynamically adjust the parameter(s) 42 used to treat textiles 12 with an antimicrobial agent for each laundry cycle based on specific conditions and/or characteristics of the textiles 12 in the laundry cycle.

As examples, the parameter(s) 42 can include the textile can include data representing (i) a concentration of a treatment solution to be applied to the textile during the laundry cycle, (ii) an amount of time the textile is to be treated, (iii) a rate of addition of the antimicrobial agent to form the treatment solution for treating the textile with the antimicrobial agent during the laundry cycle, (iv) an amount of detergent to be applied to the textile during the laundry cycle, (v) an amount of time the textile is to be washed in one or more modules 120A-120F of the washer system 100 during the laundry cycle, and/or (vi) an amount of time that the textile is to be agitated during the laundry cycle.

The input/output device 36 includes one more devices configured to receive inputs from and/or provide outputs to a user. For example, the input/output device 36 can include a display that is configured to output information to the user. In one implementation, the display is a touchscreen configured to output information to the user and receive user input. The input/output device 36 can additionally and/or alternatively include one or more buttons, switches, levers, microphones, etc. configured to receive user inputs and/or one or more speakers, indicator lights, etc. configured to present visual/auditory outputs to the user. As described above, the input/output device 36 is communicatively coupled to the processor 32 for receiving the inputs from the user and/or providing the outputs to the user.

FIG. 2 depicts the textile 12 with the identification tag 24 configured as a RFID tag 24A according to an example. As shown in FIG. 2, the RFID tag 24A is coupled to the textile 12. In an example, the RFID tag 24A can include an integrated circuit (IC) chip 44 that stores the identification information associated with the textile 12. The RFID tag 24A can further include an antenna (not shown) for communicating with the reader device 26 and/or a protective housing (not shown) for protecting the RFID tag 24A during use and/or a laundry cycle. For instance, the protective housing can provide a waterproof, heat resistant, and/or pressure resistant enclosure for housing the IC chip 44 and the antenna. This can facilitate protecting the RFID tag 24A from the conditions of the washer system. Within examples, the RFID tag 24A can be a passive RFID tag, a semi-passive RFID tag, and/or an active RFID tag.

In FIG. 2, the reader device 26 is a RFID interrogator having an antenna 45. Using the antenna 45, the reader device 26 can wirelessly read the unique identification information stored in the IC chip 42. For example, the reader device 26 can transmit an interrogation signal 46 to the IC chip 42 and responsively receive a radio signal 48 from the RFID tag 24A that represents the unique identification information. Within examples, the reader device 26 can be in the form of a mobile handheld device and/or a container having a receptacle for receiving multiple textiles 12.

FIG. 3 depicts the textile 12 with the identification tag 24 configured as a barcode 24B according to another example. The barcode 24B can be coded to represent the unique identification information associated with the textile 12. As shown in FIG. 3, the reader device 26 includes an optical barcode scanner 50 for transmitting and receiving optical signal 52 to read the barcode 24B and determine the unique identification information from the barcode 24B.

Figure 4:
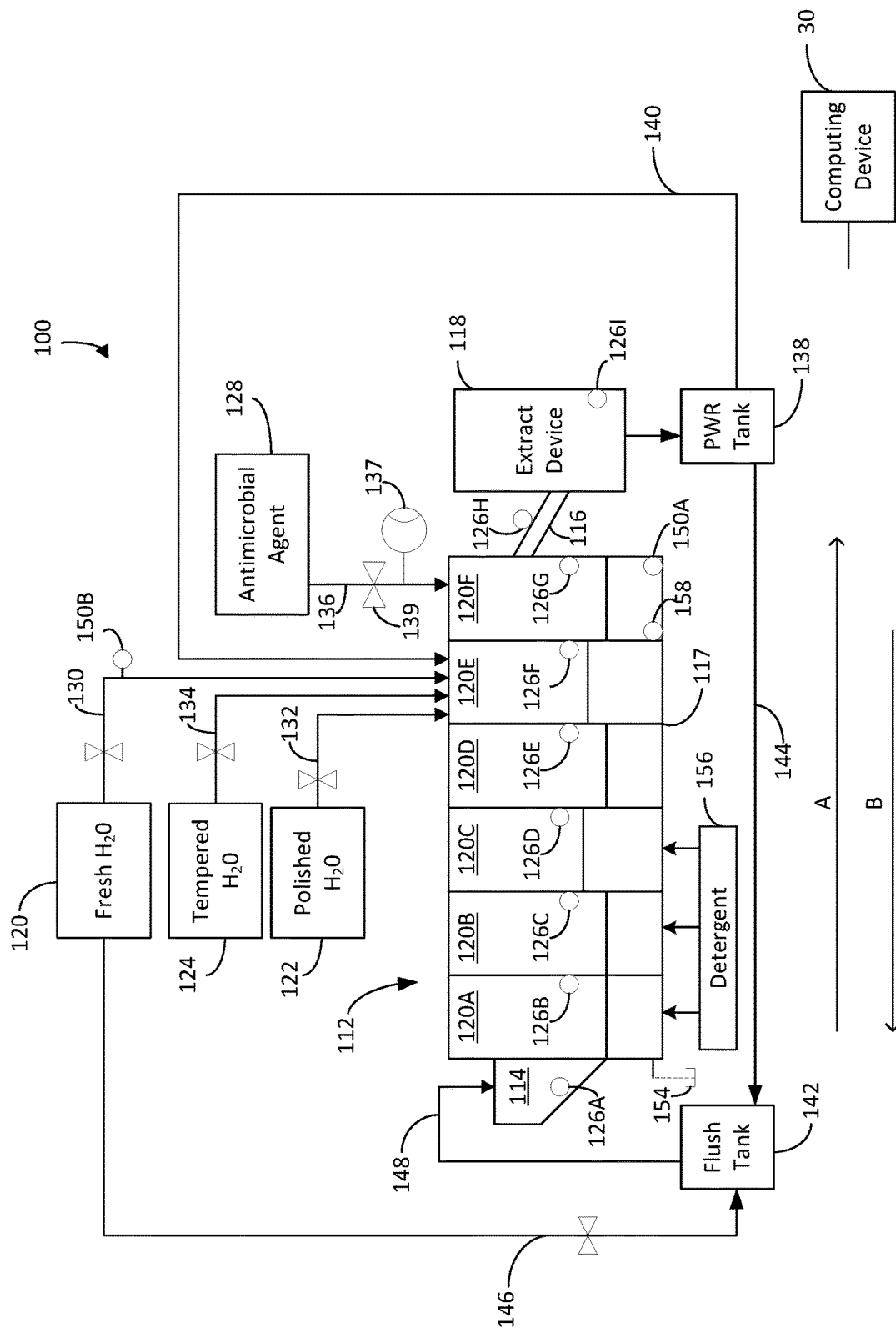
FIG. 4 is a simplified block diagram of a washer system in which a textile may be used according to an example embodiment.

Referring now to FIG. 4, a simplified block diagram of an example washer system 100 is illustrated according aspects of the disclosure. As shown in FIG. 4, the washer system 100 includes a tunnel washer 112 having an intake 114 at a first end and a discharge 116 at a second end. The intake 114 receives one or more textiles to be washed and treated. In one example, the intake 114 can be in the form of a hopper that can receive a batch of textiles into the tunnel washer 112. The discharge 116 facilitates transferring clean, treated textiles from the tunnel washer 112 to a fluid-extraction device 118. In one example, the discharge 116 can be in the form of a slide or a chute that transports the washed textiles towards the fluid-extraction device 118. In another example, the discharge 116 can include a receptacle for holding the washed textiles until the fluid-extraction device 118 is ready to receive the washed textiles. The fluid-extraction device 118 can be, for example, a centrifugal extractor and/or a mechanical press.

The tunnel washer 112 includes an outer housing 117, which defines an interior of the tunnel washer 112. The interior of the tunnel washer 112 is segmented by a plurality of modules 120A-120F between the intake 114 and the discharge 116. In the illustrated example, the modules 120A-120F are formed as a plurality of rotating drums separated from each other by lateral side walls.

During operation, the textiles to be washed and treated sequentially move through the modules 120A-120F in the direction of arrow A, entering the outer housing 117 at the intake 114 and exiting the outer housing 117 at the discharge 116. To do so, the modules 120A-120F transfer textiles from one module to the next by a top transfer arrangement and/or a bottom transfer arrangement. For example, the drums may have inlets and outlets on opposing sides of the drums so that the textiles may be transferred through the outlet in one drum into the inlet in the next drum. In some implementations, each drum can further include a scoop-like member mounted within the drum to facilitate transferring the textiles via the inlets and outlets. The scoop-like members can be configured such that oscillating the drums within a limited range of rotation does not transfer the textiles between drums, but instead imparts mechanical action to the textiles to promote the wash and treatment process. However, when the drums are rotated beyond the limited range of rotation, the scoop-like members receive and transport the textiles to the outlets of the drums. In this way, the textiles entering the tunnel washer 112 at the intake 114 are transported through each of the modules 120A-120F in sequence to the discharge 116.

Although the modules 120A-120F are described as rotating drums in the above example, it should be understood that the modules 120A-120F can be formed in other ways such as, for example, by an Archimedean screw within the outer housing 117. Additionally, it should be understood that the modules 120A-120F can have a single-drum construction (i.e., a single drum containing both the fluids and the textiles), a double-drum construction (i.e., each module has a stationary, exterior drum to hold fluids and a rotating, perforated inner drum to move textiles in the fluids), or a combination of single- and double-drum constructions.

In practice, the tunnel washer 112 can include one or more pre-wash modules, one or more main wash modules, one or more rinse modules, one or more neutralization modules, and/or one or more treatment modules according to aspects of the disclosure. The pre-wash module(s) define a pre-wash zone of the tunnel washer 112, the main wash module(s) define a main wash zone, the rinse module(s) define a rinse zone, the neutralization module(s) define a neutralization zone, and the treatment module(s) define a treatment zone of the tunnel washer 112. The number of modules utilized to form these zones in the tunnel washer 112 may vary in different example implementations.

In the illustrated example, the tunnel washer 112 has a pre-wash zone provided by the intake 114 as described in further detail below. The pre-wash zone facilitates initial wetting of the textiles and, optionally, applying heat and wash chemistry early in the process to remove soil from the textiles prior to entering the main wash zone. The tunnel washer 112 has a main wash zone formed by a first module 120A, a second module 120B, and a third module 120C. The modules 120A-120C of the main wash zone may apply heat, steam, wash agents (e.g., a detergent, alkali, bleach, etc.), and/or mechanical action to facilitate removing soil from the textiles. The tunnel washer 112 next includes a rinse zone formed by a fourth module 120D and a fifth module 120E. The modules 120D-120E of the rinse zone facilitate removing residual wash agents carried over during transfer of the textiles from the main wash zone. The tunnel washer 112 lastly includes a treatment zone formed by a sixth module 120F in which the textiles are treated with the antimicrobial agent.

By treating the textile with the antimicrobial agent in the last module 120F before the discharge 116, greater amounts of antimicrobial agent are retained by the textile upon completion of the laundry cycle. This is, in part, because treating the textile in the last module 120F mitigates leaching of antimicrobial agent content from the textile, which would otherwise occur if the textile was further washed or rinsed after being treated with the antimicrobial agent. In other embodiments, the rinse module and treatment module are combined, such that rinsing the textiles and treating the textiles with an antimicrobial agent occurs in the same module or modules. Indeed, in some aspects, the solution used to treat the textiles also performs the functions of a rinse to remove residual wash agents from the textiles.

Although the illustrated example has six modules, it should be understood that the tunnel washer 112 can have more or fewer modules according to alternative aspects of the disclosure. For instance, in some alternative examples, the tunnel washer 112 can have eight to twelve modules. It also should be understood that, in some alternative examples, the pre-wash functions can be provided in one or more pre-wash module(s) instead of the intake 114. And it should be understood that, in some alternative examples, the tunnel washer 112 can include a neutralization zone, between the rinse zone and the treatment zone, to facilitate neutralizing residual alkali, detergent, and/or bleach carried over during transfer of the textiles from the rinse zone. In some examples, the neutralization zone may be further utilized to apply a softener and/or starch to the textiles.

To facilitate adding, removing, and/or transferring water and chemicals in the modules 120A-120F, the tunnel washer 112 can include one or more drains, water sources, chemical sources, fluid tanks, flow lines, valves, pumps, nozzles, and/or weir plates. In the illustrated example, the washer system 100 includes a fresh water source 122, a polished water source 124, and a tempered water source 124. The fresh water source 122 can provide, for example, cold fresh water (e.g., water supplied by a municipality). The polished water source 124 can provide water treated by one or more filtration processes such as, for example, a deionization process, a reverse osmosis process, a granulated activated carbon (GAC) filtration process, a distillation process, or a combination thereof. The tempered water source 124 can provide water that has been heated, for example, to a temperature between approximately 85 degrees Fahrenheit and approximately 100 degrees Fahrenheit (i.e., between approximately 29 degrees Celsius and 43 degrees Celsius).

Also, in the illustrated example, a flow line 130 provides fresh water from the fresh water source 122 to the fifth module 120E, a flow line 132 provides polished water from the polished water source 124 to the fifth module 120E, and a flow line 134 provides tempered water from the tempered water source 124 to the fifth module 120E. Although the flow lines 130, 132, 134 are illustrated as separate from one another, one or more of the flow lines 130, 132, 134 may be coupled so as to provide a mixture of fresh water, polished water, and/or tempered water to the fifth module 120E in other examples. In general, the amount and/or composition of fluid supplied by the sources 120, 122, 124 at a given time may be based on various criteria such as, for example, a measurement of an amount of total dissolved solids (TDS), a hardness, an anions species, etc. by one or more sensors (not shown) in one or more modules 120A-120E.

To supply the modules 120A-120D with fluids, the tunnel washer 112 counterflows fluids from the fifth module 120E towards the intake 114. In this way, the textiles continuously encounter cleaner fluids as the textiles are progressed through the tunnel washer 112 from the intake 114 to the discharge 116. Depending on the construction of the modules 120A-120E, the tunnel washer 112 may transfer fluids by direct counterflow (e.g., fluid flowing through or over lateral side walls due to gravity) and/or indirect counterflow (e.g., via external flow lines and pumps between the modules 120A-120E). Commercially available examples of indirect counterflow systems are the CBW® Tunnel Washer and the PBW® Tunnel Washer, including PULSEFLOW® technology (Pellerin Milnor Corporation, Kenner, La.).

In the illustrated example, a combination of direct counterflow and indirect counterflow can be employed to achieve example fluid levels shown in FIG. 4 for each module 120A-120E. In particular, direct counterflow is utilized for transferring fluids within the rinse zone and for transferring fluids within the main wash zone, whereas indirect counterflow is utilized for transferring fluids from the treatment zone or rinse zone to the main wash zone. This arrangement may help to separate the rinse and wash zones.

In one non-limiting implementation of the illustrated example, the fluid within the fifth module 120E can counterflow back to the fourth module 120D via a weir plate (not shown). The fluid within the fourth module 120D can counterflow back to the third module 120C via a pump (not shown). Using a pump allows the fluid level in the third module 120C to be higher than the fluid level in the fourth module 120D, as shown in FIG. 4. The fluid in the third module 120C then can counterflow back to the second module 120B and the fluid in the second module 120B can counterflow back to the first module 120A via weir plates. The first module 120A may include a weir plate that facilitates transferring excess fluids in the first module 120A to a drain 154. It should be understood that other example implementations for counterflowing fluids from the fifth module 120E to the first module 120A are possible.

The washer system 100 also includes an antimicrobial agent source 128. The antimicrobial agent source 128 can include any device suitable for holding and/or supplying an antimicrobial agent to the tunnel washer 112. Example devices and processes for supplying the antimicrobial agent to the tunnel washer 112 are described in U.S. Pat. No. 8,641,967, U.S. Patent Appl. Publication No. 2015/0159314, Patent Appl. Publication No. 2015/0159319, Patent Appl. Publication No. 2015/0047718, and U.S. application Ser. No. 13/968,084 filed Aug. 15, 2013, the contents of which are incorporated by reference in their entirety. In some of such examples, the antimicrobial source 128 may dilute the antimicrobial agent from a first concentration to a second, lower concentration prior to supplying the antimicrobial agent to the tunnel washer 112. In other examples, the antimicrobial agent can be received in the antimicrobial agent source 128 in the same concentration in which it is supplied to the tunnel washer 128.

In some aspects, the antimicrobial agent can include a metallic ion such as, for example, silver ions. For instance, the antimicrobial agent can include silver nitrate, silver acetate, silver oxide, silver chloride, silver carbonate, silver sulfate, etc. One benefit to using an antimicrobial agent including silver ions is that such antimicrobial agents may cause less skin irritation and may be less detectable by a user than other antimicrobial agents. Nonetheless, it should be understood that other antimicrobial agents can be utilized such as, for example, other metallic ions (e.g., copper, zinc, etc.). The washer system 100 further includes a flow line 136 for providing an antimicrobial solution (i.e., a treatment solution) from the antimicrobial agent source 128 to the sixth module 120F. The treatment solution may include a concentration of antimicrobial agent. A flow meter 137 and a flow control device 139 can be coupled to the flow line 136 to respectively monitor and control the amount of treatment solution (and, thus, the amount of antimicrobial agent) that is provided from the antimicrobial source 128 to the sixth module 120F. The flow control device 139 can include, for example, a peristaltic pump, a diaphragm pump, a solenoid valve, etc.

The sixth module 120F may be initially filled with a combination of fresh water and treatment solution from the fresh water source 122 and the antimicrobial agent source 128, respectively. A flow line from the fresh water source 122 to the sixth module 120F is omitted for clarity of illustration. After the initial setup, additional fluids may be supplied to the sixth module 120F via the transfer of textiles from the fifth module 120E and the antimicrobial agent source 128.

In one aspect, the treatment solution from the antimicrobial agent source 128 is added to fresh water or other process water in the treatment module 120F. The concentration of the antimicrobial agent (i.e., the dosage of antimicrobial agent) applied to textiles in the module 120F may be expressed in terms of mg of antimicrobial agent per Kg of textile in the module 120F (i.e., a dry weight concentration) or, alternatively, in terms of parts per million (PPM) in an aqueous solution (i.e., a liquid concentration). In some examples, the treatment solution can be controllably added to the module 120F to achieve a concentration of approximately 0.5 to approximately 50 mg of antimicrobial agent per 1 Kg of textile in the module 120F. In other examples, the antimicrobial agent can be applied to textiles at a concentration greater than approximately 8 mg antimicrobial agent per 1 Kg of textile and, in still other examples, a concentration greater than approximately 10 mg antimicrobial agent per 1 Kg of textile.

As shown in FIG. 4, the washer system 100 includes a plurality of reader devices 126A-126I at a plurality of locations in the washer system 100. The reader devices 126A-126I include a first reader device 126A at the intake 114, a second reader device 126B at the first module 120A, a third reader device 126C at the second module 120B, a fourth reader device 126D at the third module 120C, a fifth reader device 126E at the fourth module 120D, a sixth reader device 126F at the fifth module 120E, a seventh reader device 126G at the sixth module 120F, an eighth reader device 126H at the discharge 116, and a ninth reader device 126I at the extract device 118. The reader devices 126A-126I are communicatively coupled to the computing device 30. The reader devices 126A-126I can detect the identification tag 24 of the textile 12 and responsively transmit signals to the computing device 30 to facilitate tracking the textile 12 as it enters, moves through, and/or exits the washer system 100.

Within examples, when the computing device 30 receives a signal identifying the textile 12 (e.g., via the identification information), the computing device 30 determines one or more parameters 42 for washing and/or treating the textile 12 in the washer system 100. For instance, the computing device 30 can use the received identification information to lookup the tracking data 36 and/or the product data 38 stored in the data storage unit 34 for the textile 12. The computing device 30 can then process the associated tracking data 36 and/or product data 38 to determine the parameter(s) 42 for washing and/or treating the textile 12. In examples in which multiple textiles 12 are to be washed and/or treated together as a batch, the computing device 30 can determine the parameter(s) 42 based on an analysis of a combination of the tracking data 36 and/or product data 38 of all of the textiles 12 in the batch, which are identified by the reader devices 126A-126I.

As an example, the computing device 30 can receive a signal from the reader device 126A, which includes the unique identification information of the identification tag 24 associated with the textile 12. The computing device 30 can then determine, based on the tracking data 36 and/or the product data 38 associated with the textile 12, a concentration of the antimicrobial agent to use in a treatment solution for treating the textile 12. The computing device 30 can then transmit a control signal to cause the antimicrobial agent source 128 and/or the flow control device 139 to provide the treatment solution with the determined concentration of the antimicrobial agent to the sixth module 120F when the textile 12 is present in the sixth module 120F. For instance, the computing device 30 can provide control signals to the flow control device 139 to cause the flow control device 139 to increase the antimicrobial agent in the sixth module 120F so as to achieve the determined dosage of antimicrobial agent.

To determine an amount of antimicrobial agent to add to the sixth module 120F, the washer system 100 can include a conductivity measurement probe 158 in the sixth module 120F. The conductivity probe 158 can measure a conductivity of the fluid in the sixth module 120F, which can provide an indication of the amount of antimicrobial agent in the fluid. The computing device 30 can be communicatively coupled to the conductivity measurement probe 158, receive signals indicating the measured conductivity, determine the amount of antimicrobial agent in the sixth module 120F based on the received signals, and then determine the amount of antimicrobial agent that needs to be added from the antimicrobial agent source 128 to achieve the determined dosage. In one example, the determined dosage can be a dosage that is expected to achieve a target level of efficacy as a result of the treatment cycle.

As an additional or alternative example, the computing device 30 can determine the rate of addition of the treatment solution to the module (i.e., the dosing rate) based on the tracking data 36 and/or the product data 38. In one implementation, the rate of addition of the treatment solution to the module can be controlled to ensure that the textile in the module is uniformly treated. In some examples, the treatment cycle lasts between about 30 seconds and about 2.5 minutes. Therefore, to achieve a uniform dose of agent throughout the textile load, the addition of the treatment solution to the module may be affected prior to the first 90 seconds of the treatment cycle.

In some aspects, the computing device 30 can cause the treatment solution to be added to the module at a fixed rate. As one example, the treatment solution having a concentration of about 2,000 PPM (aq) to about 15,000 PPM (aq), more particularly about 4000-15000 PPM, is added to a treatment module containing about, for example, 600 liters of liquid and 150 Kg of textile at a rate of about 30 ml/minute for about 2.5 minutes. In other examples, the antimicrobial agent can be added to the module at a rate between about 5 ml/min to about 50 ml/min for a period of time between about 15 seconds to about 150 seconds. In one particular non limiting example, a 600 liter liquid bath having a liquid antimicrobial agent concentration of 2 PPM (aq) is achieved by adding a 1000 ml solution having an agent concentration of 1,200 PPM for 2.5 minute at rate of 400 ml/min. At this concentration, assuming a theoretical 100% yield, the textiles would be infused with 8 mg/kg of antimicrobial agent.

In other aspects, the computing device 30 can cause the treatment solution to be added to the module at a variable rate, which further improves the uniformity of the antimicrobial agent on the finished textile. In one example, the antimicrobial agent can be added to the module containing 600 liters of liquid at a rate of about 5 ml/min for about 15 seconds to about 60 seconds followed by a rate of about 20 ml/min for about 15 seconds to about 90 seconds.

As another example, the computing device 30 can determine the concentration utilized for a textile based on product data 38 indicating the type of textile material in the textile as different materials may have different uptake yield rates, which reflects the percent of the antimicrobial agent that becomes associated with the textile during the treatment. Table 1 illustrates example yields for example dosages of textiles of different materials.

TABLE 1

| Linen Type | Batch | Dosage (mg/kg) | Silver Content (mg/kg) | | | | Yield (%) |
| | | | 1 | 2 | 3 | AVG | |
|---|---|---|---|---|---|---|---|
| Cotton | Lot 1 | 1 | 1.1 | 0.8 | 1.3 | 1.1 | 107 |
| | Lot 2 | 1 | 0.7 | 0.8 | 0.7 | 0.7 | 73 |
| | Lot 3 | 1 | 0.7 | 0.7 | 0.8 | 0.7 | 73 |
| Cotton/Poly Blend | Lot 1 | 1.5 | 1.1 | 1.0 | 1.1 | 1.1 | 71 |
| | Lot 2 | 1.5 | 0.9 | 1.9 | 2.9 | 1.9 | 127 |
| | Lot 3 | 1 | 0.9 | 0.9 | 0.9 | 0.9 | 90 |

TABLE 1-continued

| Linen Type | Batch | Dosage (mg/kg) | Silver Content (mg/kg) | | | | Yield (%) |
|---|---|---|---|---|---|---|---|
| | | | 1 | 2 | 3 | AVG | |
| Spandex | Lot 1 | 3.4 | 1.4 | 1.6 | 1.6 | 1.5 | 45 |
| | Lot 2 | 3.4 | 1.5 | 1.7 | 1.6 | 1.6 | 47 |
| | Lot 3 | 3.4 | 1.6 | 1.6 | 1.6 | 1.6 | 47 |
| Polyester | Lot 1 | 3.4 | nd | 0.6 | nd | 0.6 | 18 |
| | Lot 2 | 3.4 | 0.7 | 0.8 | 0.6 | 0.7 | 21 |
| | Lot 3 | 3.4 | 1 | 0.9 | 0.9 | 0.9 | 27 |
| | Lot 4 | 4 | 0.9 | 0.9 | 0.9 | 0.9 | 23 |
| Nylon | Lot 1 | 35 | 1.6 | 1.8 | 1.5 | 1.6 | 5 |
| Spandex | Lot 2 | 35 | 1.4 | 1.3 | 1.4 | 1.4 | 4 |
| Blend | Lot 3 | 35 | 1.2 | 1.4 | 1.3 | 1.3 | 4 |
| 100% | Lot 1 | 35 | 0.9 | 0.9 | 0.9 | 0.9 | 3 |
| Nylon | Lot 2 | 35 | 0.9 | 0.8 | 0.8 | 0.8 | 2 |
| | Lot 3 | 35 | 1 | 0.9 | 1.1 | 1.0 | 3 |
| 100% | Lot 1 | 35 | 0.7 | 0.6 | 0.7 | 0.7 | 2 |
| Microfiber | Lot 2 | 35 | 0.5 | 0.6 | 0.6 | 0.6 | 2 |
| | Lot 3 | 35 | 0.9 | 0.8 | 0.7 | 0.8 | 2 |

In Table 1, the dosage reflects the amount of silver ion per kg of textile in the each batch of a treatment cycle a pilot plant study. Silver nitrate was added in an amount that provides the appropriate ion weight. The volume of batch liquid was approximately 25 liters and the amount of the textile was approximately 0.25 kg. It should be understood that Table 1 reflects exemplary dosage values that can be used for the textile materials shown, and other dosages are contemplated For example, in some implementations, a batch of textiles of a particular material may be dosed at a dosage value that differs by about plus or minus 50% from the dosage value listed in Table 1 for the same material, depending on the desired silver content of the treated textile and/or the target antimicrobial efficacy sought to be achieved. Other example implementations are also possible.

In general, the volume of the liquid in each batch may not be critical to the antimicrobial update (yield) by the textile. Typically, industrial applications involve treatment batch sizes of about 500-1000 liters, for example about 600 L, for textile loads of about 150 kg. It has been found that moderate adjustment of the liquid volume of the treatment batch does not substantially affect yield.

As noted above, the reader devices 126A-126I are communicatively coupled to the computing device 30. As such, each reader device 126A-126I can transmit a signal to the computing device 30 responsive to the reader device 126A-126I detecting the identification tag 24. Responsive to the computing device 30 receiving the signal, the computing device 30 can determine and/or update tracking data for the textile 12 based on the unique identification information. For instance, the computing device 30 can record the time at which the textile was present within the modules 120A-120F. The computing device 30 can also record the parameter(s) 42 used to wash and/or treat the textile 12 during that the recorded times of the textile 12. In this way, the computing device 30 can determine additional information about how the textile 12 was washed and/or treated so that subsequent laundry cycles can be dynamically controlled based on the events of the present laundry cycle (and other past laundry cycles).

As noted above, after the textiles are treated in the sixth module 120F, the textiles are transferred to the fluid-extraction device 118 via the discharge 116. The fluid-extraction device 118 extracts fluids from the textiles. In some examples, the extracted fluids may be drained as waste water effluent. One problem with such an approach is that the extracted fluids may contain excess antimicrobial agent that was not retained within the textiles. If the effluent is not treated, the excess antimicrobial agent may be released into waterways. Above certain concentrations, antimicrobial agents may be a problematic pollutant for many fresh- and salt-water organisms. For this reason, many governmental regulations require operators to treat effluent if the concentration of antimicrobial agent is greater than a proscribed limit (e.g., 10 mg per kg). Unfortunately, effluent treatment can be prohibitively expensive for many laundry operators. Additionally, in some instances, draining the extracted fluids may unnecessarily waste substantial amounts of antimicrobial agent, increasing the cost to treat textiles.

According to some aspects of the disclosure, the washer system 100 can address these problems associated with excess antimicrobial agent in the extracted fluids. In particular, the washer system 100 can collect the extracted fluids from the fluid-extraction device 118 and recirculate the extracted fluids back into the tunnel washer 112. Advantageously, recirculating the extracted fluids mitigates wasted antimicrobial agent and the extent to which waste water effluent needs to be treated to comply with environmental regulations.

In the illustrated example, the extracted fluids are collected in a press-water-recovery (PWR) tank 138. As shown in FIG. 4, the PWR tank 138 can provide at least a portion of the extracted fluid to the fifth module 120E in the rinse zone via a flow line 140. Providing antimicrobial agent (e.g., silver ions) to a module 120E preceding the treatment module 120F may allow the antimicrobial agent to bind or chelate to contaminants or other inhibiting ions in the fluid of module 120E, thereby facilitating a more accurate treatment of the textiles in the treatment module 120F. Additionally, providing the antimicrobial agent to the module 120E may facilitate greater uniformity of antimicrobial agent distribution in the textiles.

Also, as shown in FIG. 4, the PWR tank 138 can also provide at least a portion of the extracted fluid to a flush tank 142 via a flow line 144. The flush tank 142 may also receive fresh water from the fresh water source 122 via a flow line 146. The flush tank 142 may then provide a mixture of fresh water and the extracted water (which may contain excess antimicrobial agent) to the intake 114 via a flow line 148. In this way, the flush tank 142 can provide fluids to the intake 114, which allow the intake 114 to function as a pre-wash module when textiles are received in the intake 114. Providing the antimicrobial agent in the intake 114 can facilitate uniformity of antimicrobial agent distribution and more accurate treatment of the textiles in subsequent modules. In general, increasing the number of exposures of the textile to the antimicrobial agent can facilitate improving the uniformity of antimicrobial agent distribution in the textile.

To provide the extracted fluids to the fifth module 150E and/or the flush tank 142, the washer system 100 can include one or more pumps and/or valves (which are not shown for clarity of illustration). Although the extracted fluids may be provided to the intake 114 and/or the fifth module 120E in the illustrated example, it should be understood that the extracted fluids can be similarly provided to other modules in other examples. For instance, in another example, at least portion of the extracted fluids can be additionally or alternatively provided by the PWR tank 138 to the sixth module 120F in the treatment zone.

According to additional or alternative aspects of the disclosure, the washer system 100 can include additional features that help to mitigate problems associated with poor water quality. During the treatment process, the metallic ions of the antimicrobial agent may attach to a textile via electrostatic dipole interactions or other interactions including mechanical interaction. For some fabrics, the positive charge from the metallic ions is attracted to the slight-negative dipole on the polymer backbone of textile fibers. Generally, contaminants present in poor quality water reduce the probability that the antimicrobial metallic ions will affix to bonding sites of the textile. This is, in part, because some metallic ions may affix to cationic contaminants instead of the textile. Thus, to achieve a desired level of antimicrobial agent content in the textiles, the textiles may need to be treated with greater amounts of antimicrobial agent when water quality is poor as compared to when water quality is good.

To address problems associated with poor or changed quality water, the washer system 100 can include one or more sensors that measure a quality of water in the system 100 and, based on the measured water quality, dynamically control the amount of antimicrobial agent utilized in a treatment cycle. For example, in the washer system 100 shown in FIG. 4, a first water quality sensor 150A is located in the sixth module 120F and a second water quality sensor 150B is located along the flow line 130. The water quality sensors 150A, 150B can be communicatively coupled to the computing device 30. In this way, the water quality sensors 150A, 150B may measure the quality of water in the sixth module 120F and the flow line 130, respectively, and transmit a water-quality signal to the computing device 30 indicating the measured water quality. The computing system 30 can thus determine and/or update the tracking data 36 based on the measured water quality in some examples. A commercially available example of a water quality sensor is the EXAxt SC450 Conductivity/Resistivity Analyser (Yokogawa North America, Inc., Sugar Land, Tex.). The computing device 30 may then process the water-quality signals to determine an amount of antimicrobial agent to be used for a treatment cycles or a plurality of treatment cycles.

Figure 5:
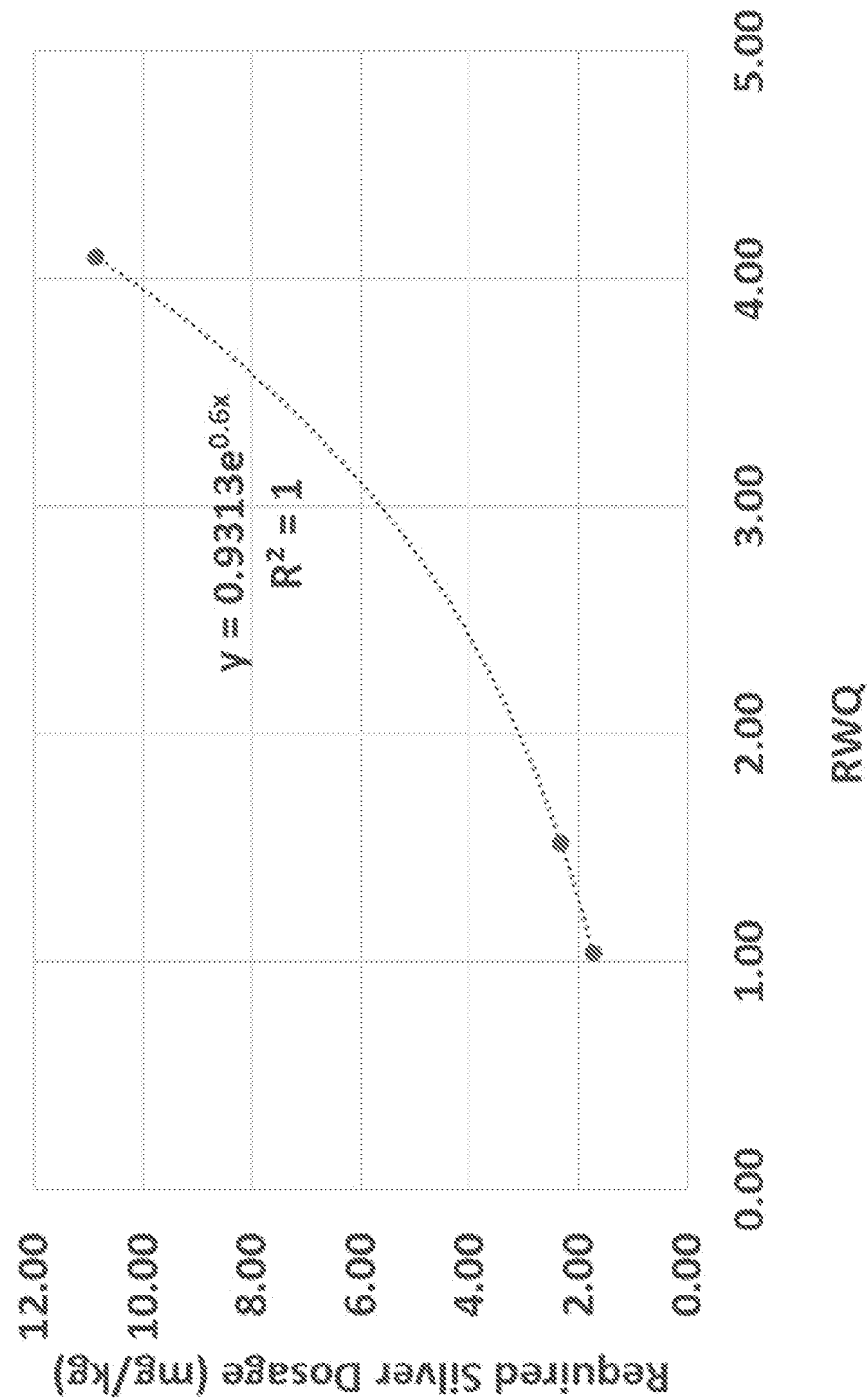
FIG. 5 is a chart illustrating an example model for determining an antimicrobial dosage based on measured water quality according to an example embodiment.

In some examples, the sensors 150A, 150B can measure one or more water quality parameters such as, for instance, a water hardness (e.g., a calcium and/or magnesium concentration), a pH, and/or a total dissolved solids (TDS) concentration. The measured water quality parameters may be weighted and combined by the computing device 30 to generate a Relative Water Quality (RWQ) number. In one implementation, a higher RWQ may indicate a higher hardness, TDS level, and/or pH. It has been discovered that as the RWQ increases, an exponentially higher dosage of antimicrobial agent is required to maintain or achieve an efficacious level of antimicrobial agent in the textiles. As such, the computing device 30 can be configured to apply one or more algorithms with the RWQ as an input and an antimicrobial dosage as an output. A chart illustrating one example algorithm for determining a dosage of antimicrobial agent (mg antimicrobial agent to Kg textile) based on measured water quality is shown in FIG. 5. It should be understood that other examples are also possible.

In an alternative aspect to address water quality, the system can add polished water to the system prior to the textiles entering the treatment zone. Accordingly prior to the textiles entering the treatment zone, the textiles are subjected to polished water. By the time the textiles enter the treatment zone, water of poor quality associated with the textiles is replaced with polished water, therefore enhancing the effectiveness of the treatment zone.

Although illustrated example includes a water quality sensor 150A in the sixth module 120F and a water quality sensor 150B in the flow line 130, it should be understood that the washer system 100 can include more or fewer water quality sensors in other examples.

Although not shown in FIG. 4 for clarity of illustration, the washer system 100 can further include a user interface to facilitate interaction with a user of washer system 100, if applicable. As such, the user interface may include input components such as a keyboard, a keypad, a mouse, a touch-sensitive panel, a microphone, and/or a camera, and/or output components such as a display device (which, for example, may be combined with a touch-sensitive panel), a sound speaker, and/or a haptic feedback system.

Referring now to FIGS. 6-13B, example processes are illustrated and described for treating textiles with an antimicrobial agent according to various aspects of the disclosure. It should be understood that, according to alternative aspects of the disclosure, the processes of FIGS. 6-13B can omit steps, include additional steps, and/or modify the order of steps presented above. Additionally, it is contemplated that one or more of the steps presented below can be performed simultaneously. It should also be understood that the example processes of FIGS. 6-13B can correspond to at least some instructions that can be executed by the computing device 30 to perform the below described functions.

The processes of the present disclosure can also be combined with the process described in co-pending U.S. application Ser. No. 15/085,539, filed Mar. 30, 2016, which is hereby incorporated by reference in its entirety.

Figure 6:
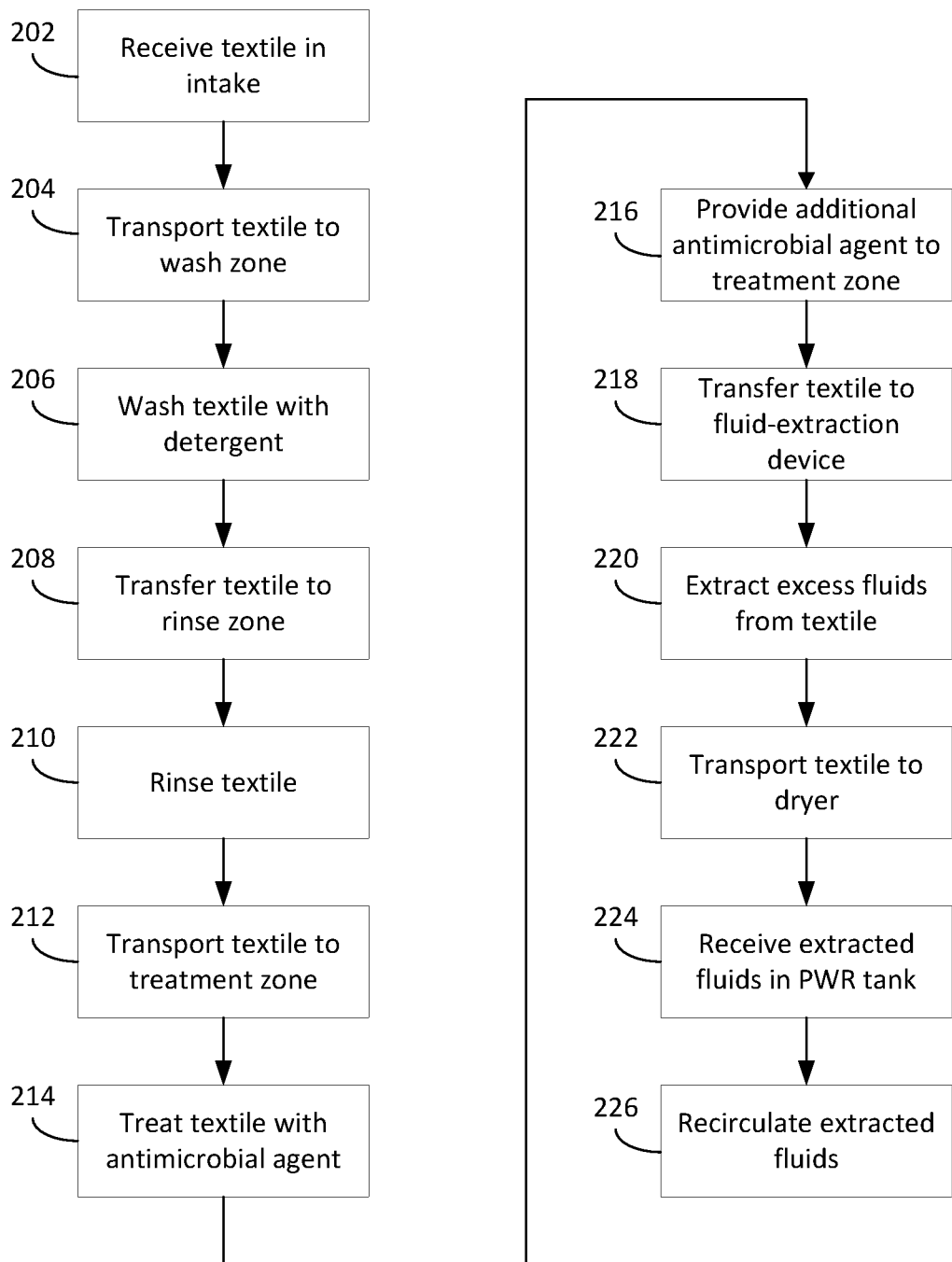
FIG. 6 is a flowchart of a process for treating textiles with an antimicrobial agent according to an example embodiment.

FIG. 6 illustrates an example flowchart for using a washer system, including a tunnel washer (e.g., the washer system 100), to treat a textile with an antimicrobial agent according to some aspects of the disclosure. At block 202, a textile is received in the intake 114. With the textile in the intake 114, the washer system 100 may provide fluid from the flush tank 142 to the intake 114 to perform a pre-wash cycle on the textile. During the pre-wash cycle, the fluid in the intake 114 may facilitate initial wetting of the textile prior to the main wash zone.

At block 204, the tunnel washer 112 transports the textile from the intake 114 to the wash zone. At block 206, the textile is washed with a detergent and, optionally, other wash chemicals, steam, and/or heat in each of the modules 120A-120C of the wash zone. The detergent can be provided to the wash zone modules 120A-120C from a detergent source 156 as shown in FIG. 4. As the textile is progressed through the modules 120A-120C, the wash fluids counterflow from the third module 120C to the first module 120A (i.e., in the direction of arrow B in FIG. 4), where excess wash fluids are drained via the drain 154.

At block 208, the textile is transferred from the wash zone to the rinse zone. In the example of FIG. 4, the textile is transferred from the third module 120C to the fourth module 120D. At block 210, the textile is rinsed in each of rinse zone modules 120D, 120E with rinse fluids provided by the fresh water source 122, the polished water source 124, and/or the tempered water source 124. Optionally, the textile may additionally or alternatively be rinsed by fluids provided by the PWR tank 138. In particular, the rinse fluids are provided to the last module 120E of the rinse zone so that the rinse fluids counterflow back to the beginning of the rinse zone at module 120D. In this way, the textile may be progressively rinsed in cleaner rinse fluids as it moves through the tunnel washer 112.

At block 212, the textile is transferred from the rinse zone to the treatment zone. In doing so, a portion of the rinse fluids may be transferred with the textile into the treatment zone module 120F. At block 214, the textile is submerged in a treatment solution including the antimicrobial agent. At block 216, the antimicrobial agent source 128 may optionally provide additional antimicrobial agent to the treatment zone module 120F (if necessary) to achieve a treatment solution having a predetermined dosage of antimicrobial agent.

At block 218, the textile is transferred, via the discharge 116, to the fluid-extraction device 118. At block 220, the fluid-extraction device 118 extracts excess fluids from the textile. At block 222, the textile may then be transported to other components for drying and/or finishing (e.g., folding).

In the example washer system 100 described above, the treatment of the textile with antimicrobial agent is described as being performed in a treatment module that is separate from the rinse modules. It should be understood that according to additional or alternative aspects, the treatment functions can be performed in the last rinse module. For example, the treatment may be performed in the last rinse module, which transfers fluids to other modules via counterflow.

At block 224, the PWR tank 138 may receive the extracted fluids from the fluid-extraction device 118. At block 226, the PWR tank 138 may recirculate at least a portion of the extracted fluids back into the tunnel washer 112. For example, the PWR tank 138 may recirculate at least a portion of the extracted fluids back to the fifth module 120E in the rinse zone (or a combined rinse/treatment zone), and/or at to the flush tank 142 for use in the intake 114 as described above.

Figure 7:
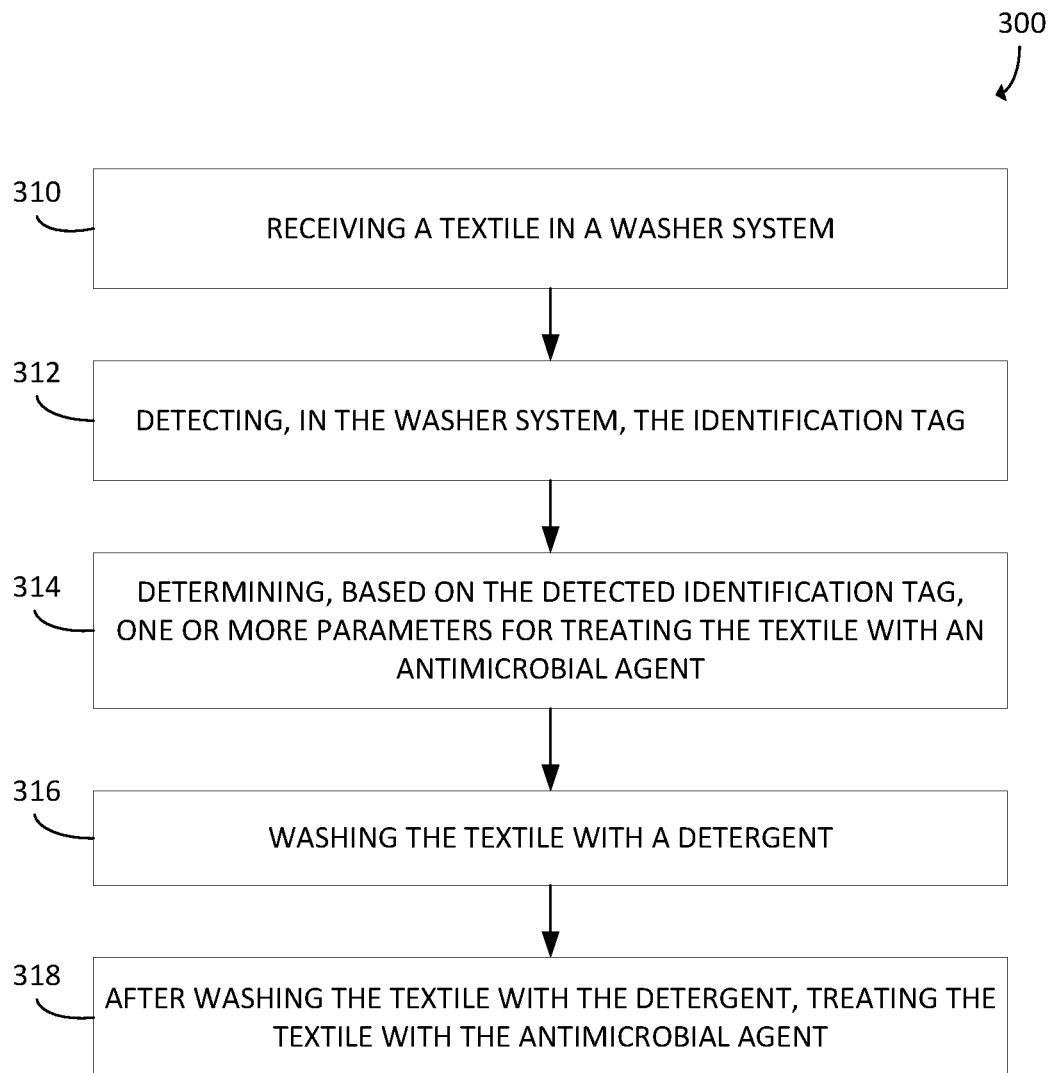
FIG. 7 is a flowchart of a process for treating textiles with an antimicrobial agent according to an example embodiment.

FIG. 7 is a flowchart of a process 300 for treating textile with an antimicrobial agent according to another example. As shown in FIG. 7, at block 310, the process 300 includes receiving a textile in a washer system. The textile includes an identification tag, which uniquely identifies the textile among a plurality of textiles.

At block 312, the process 300 includes detecting, in the washer system, the identification tag. At block 314, the process 300 includes determining, based on the detected identification tag, one or more parameters for treating the textile with an antimicrobial agent, wherein the antimicrobial agent comprises a metallic ion. At block 316, the process 300 includes washing the textile with a detergent. After washing the textile with the detergent at block 316, the process 300 includes treating the textile with the antimicrobial agent based on the one or more parameters at block 318.

Figure 8:
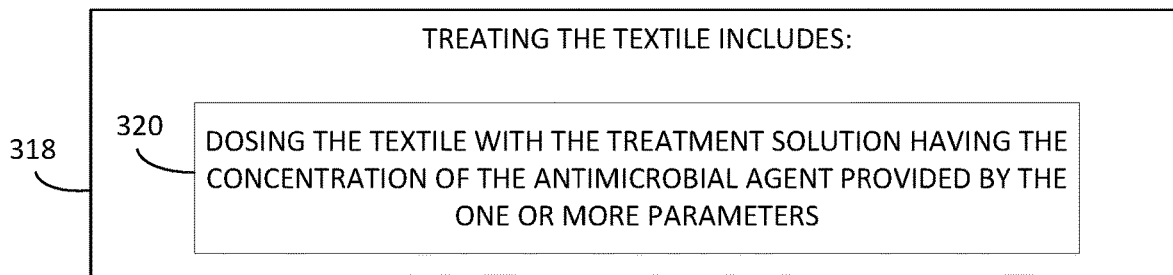
FIG. 8 is a flowchart of a process for treating textiles with an antimicrobial agent according to an example embodiment.

FIGS. 8-12 depict additional aspects of the method 300 according to further examples. In FIG. 8, the one or more parameters can provide a dosing rate for treating the textile with the antimicrobial agent, and treating the textile at block 318 can include transferring a treatment solution of the antimicrobial agent to a module of the washer system at the dosing rate provided by the one or more parameters at block 320.

Figure 9:
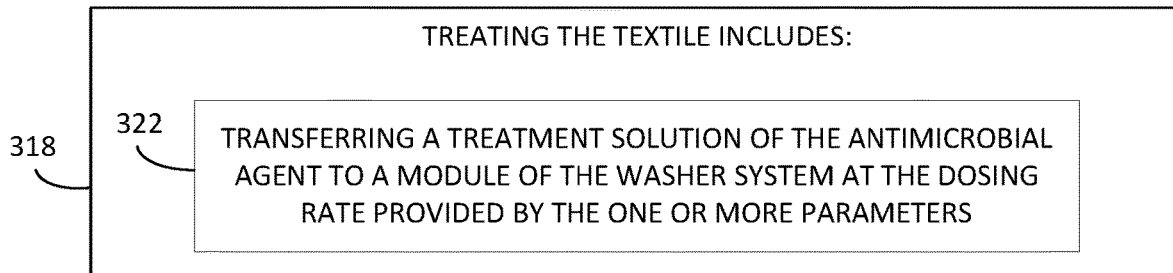
FIG. 9 is a flowchart of a process for treating textiles with an antimicrobial agent according to an example embodiment.

In FIG. 9, the one or more parameters can provide a dosing rate for treating the textile with the antimicrobial agent, and treating the textile at block 318 can include transferring a treatment solution of the antimicrobial agent to a module of the washer system at the dosing rate provided by the one or more parameters at block 322.

Figure 10:
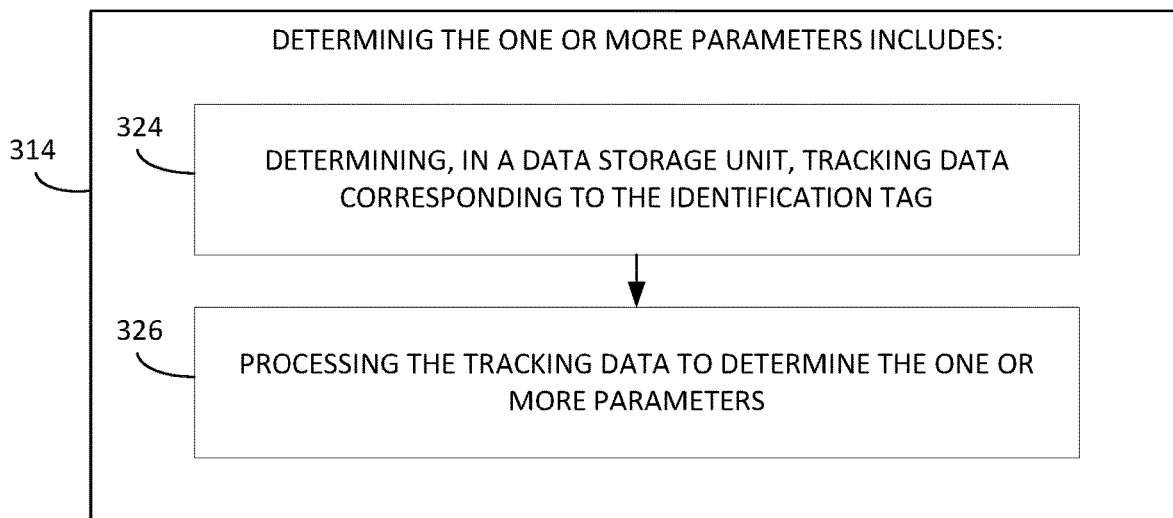
FIG. 10 is a flowchart of a process for treating textiles with an antimicrobial agent according to an example embodiment.

In FIG. 10, determining the one or more parameters at block 314 can include determining, in a data storage unit, tracking data corresponding to the identification tag at block 324. The tracking data can be based on one or more prior detections of the identification tag. Determining the one or more parameters at block 314 can also include processing the tracking data to determine the one or more parameters at block 326.

Figure 11:
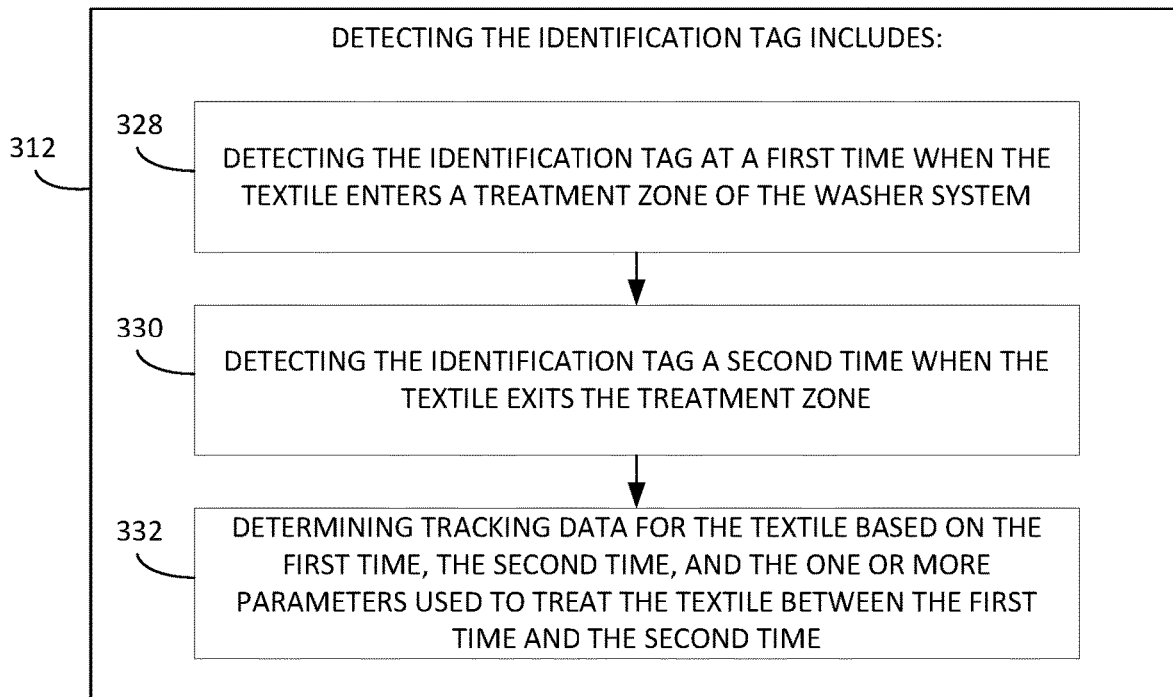
FIG. 11 is a flowchart of a process for treating textiles with an antimicrobial agent according to an example embodiment.

In FIG. 11, detecting the identification tag at block 312 can include (i) detecting the identification tag at a first time when the textile enters a treatment zone of the washer system at block 328, (ii) detecting the identification tag at a second time when the textile exits the treatment zone at block 330, and (iii) determining tracking data for the textile based on the first time, the second time, and the one or more parameters used to treat the textile between the first time and the second time at block 332.

Figure 12:
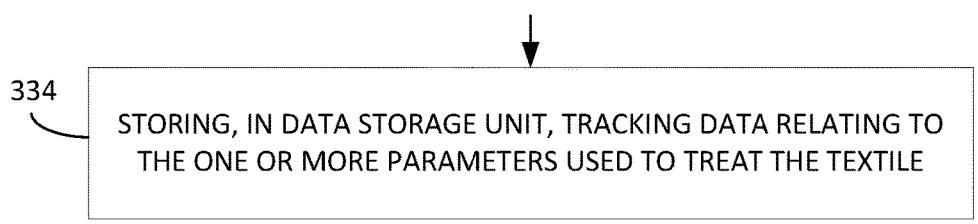
FIG. 12 is a flowchart of a process for treating textiles with an antimicrobial agent according to an example embodiment.

In FIG. 12, the process 300 can further include storing, in a data storage unit, tracking data relating to the one or more parameters used to treat the textile at block 334.

Figure 13A:
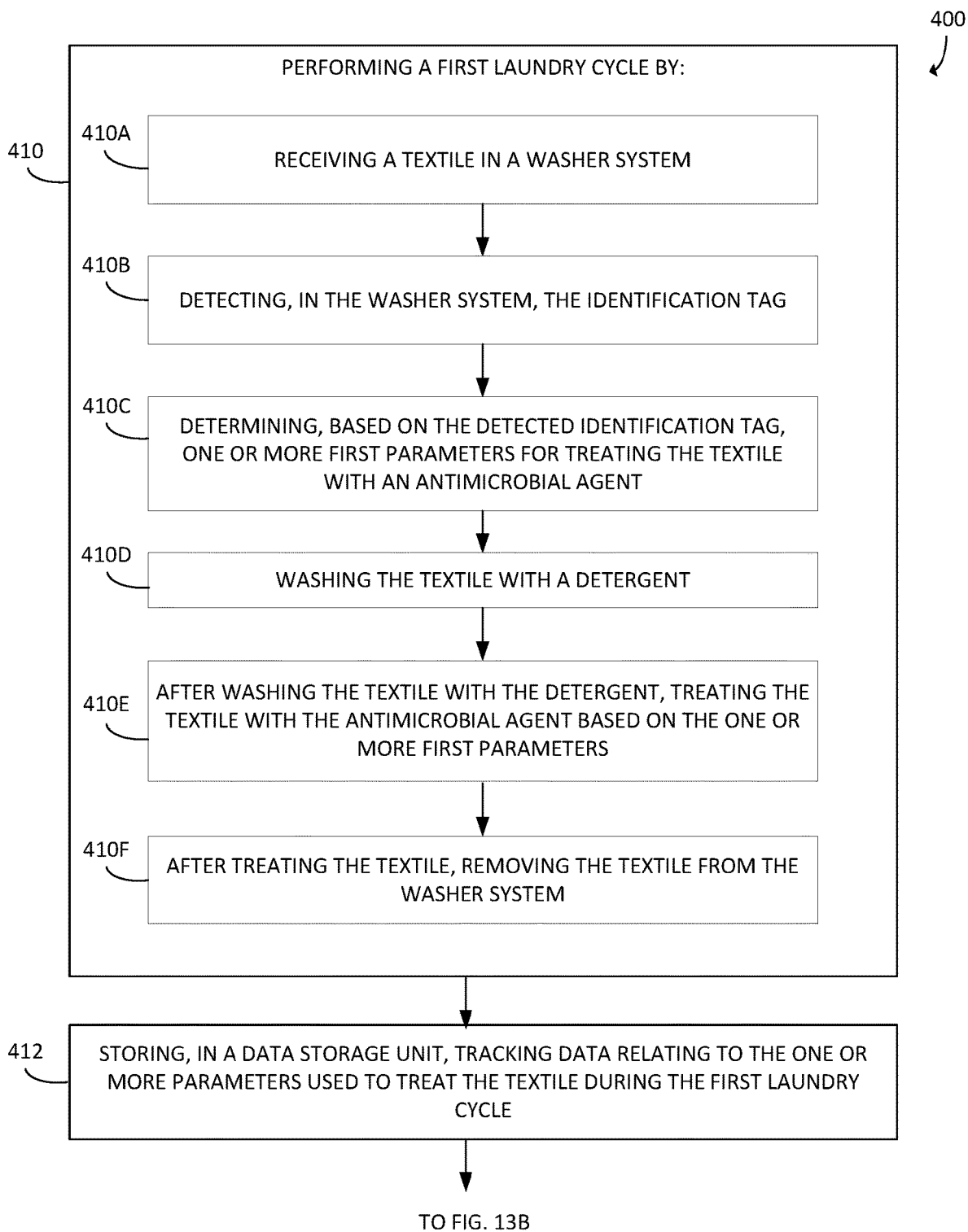
FIG. 13A is a flowchart of a process for treating textiles with an antimicrobial agent according to an example embodiment.
Figure 13B:
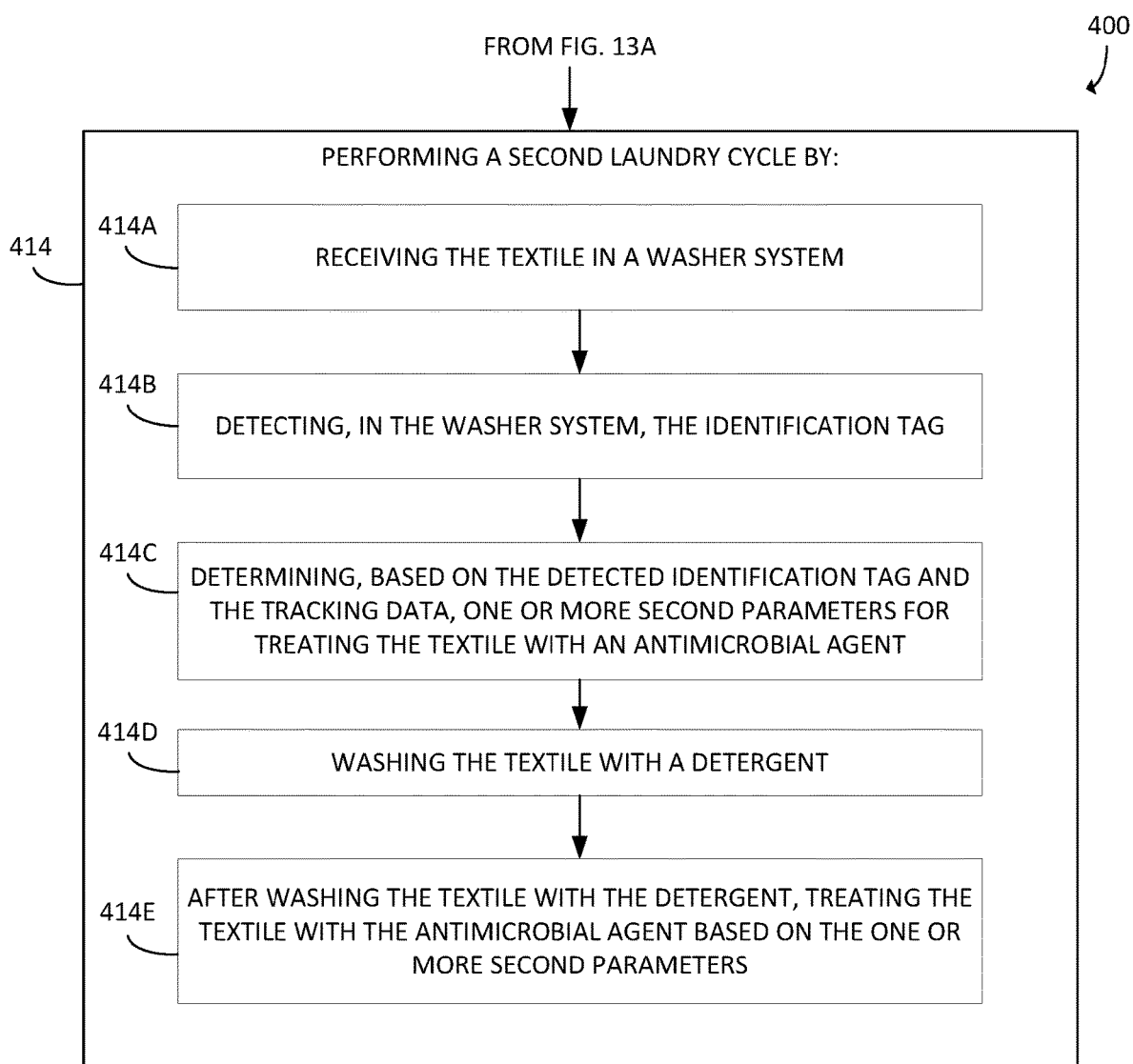
FIG. 13B is a flowchart of a process for treating textiles with an antimicrobial agent according to an example embodiment.

FIGS. 13A-13B is a flowchart of a process 400 for treating textile with an antimicrobial agent according to another example. As shown in FIGS. 13A-13B, the process 400 includes performing a first laundry process at block 410 by performing the steps shown in blocks 410A-410F. At block 410A, the process 400 includes receiving a textile in a washer system for the first laundry cycle. The textile includes an identification tag, which uniquely identifies the textile among a plurality of textiles. At block 410B, the process 400 includes detecting, in the washer system, the identification tag during the first laundry cycle. At block 410C, the process 400 includes determining, based on the detected identification tag, one or more first parameters for treating the textile with an antimicrobial agent during the first laundry cycle. The antimicrobial agent comprises a metallic ion. At block 410D, the process 400 includes washing the textile with a detergent during the first laundry cycle. After washing the textile with the detergent at block 410D, the process 400 includes treating the textile with the antimicrobial agent based on the one or more first parameters at block 410E. After treating the textile at block 410E, the process 400 includes removing the textile from the washer system at block 410F.

At block 412, the process 400 further includes storing, in a data storage unit, tracking data relating to the one or more first parameters used to treat the textile during the first laundry cycle at block 412. As also shown in FIGS. 13A-13B, after the first laundry cycle at block 410, the process 400 includes performing a second laundry cycle at block 414 by performing the steps shown in blocks 414A-414E. At block 414A, the process 400 includes receiving the textile in a washer system for the second laundry cycle. At block 414B, the process 400 includes detecting, in the washer system, the identification tag during the second laundry cycle. At block 414C, the process 400 includes determining, based on the detected identification tag and the tracking data stored in the data storage unit, one or more second parameters for treating the textile with an antimicrobial agent. At block 414D, the process 400 includes washing the textile with a detergent. After washing the textile with the detergent at block 414D, the process 400 includes treating the textile with the antimicrobial agent based on the one or more second parameters at block 414E.

Aspects of the disclosure are described above in the context of the washer system 100, which includes a tunnel washer 112 having a plurality of modules 120A-120F. However, these aspects of the disclosure can be extended to systems and processes in the context of residential and/or commercial washer-extraction devices. For example, according to alternative aspects, the one or more reader devices can be provided in a washer-extraction device, which may control an amount of antimicrobial agent utilized in a treatment cycle based on tracking data stored for the textile.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A method of treating a textile with an antimicrobial agent, the method comprising:
   detecting, in a washer system, an identification tag, wherein the identification tag uniquely identifies a textile;
   determining, based on the detected identification tag, one or more parameters for treating the textile with an antimicrobial agent, wherein the antimicrobial agent comprises a metallic ion, and wherein determining the one or more parameters comprises:
      determining tracking data corresponding to the identification tag, wherein the tracking data includes medical-related information, wherein medical-related information is a medical record associated with at least one user associated with the textile, and wherein the medical record is used to determine information relating to at least one of: (i) one or more medical procedures performed on the user; or (ii) one or more health conditions of the user for a time period during which the user used the textile; and
      processing the tracking data to determine the one or more parameters; and
   treating the textile with the antimicrobial agent based on the one or more parameters.

2. The method of claim 1, wherein the one or more parameters provide a concentration of the antimicrobial agent for a treatment solution.

3. The method of claim 2, wherein treating the textile comprises dosing the textile with the treatment solution having the concentration of the antimicrobial agent provided by the one or more parameters.

4. The method of claim 1, wherein the one or more parameters provide a dosing rate for treating the textile with the antimicrobial agent.

5. The method of claim 4, wherein treating the textile comprises transferring a treatment solution of the antimicrobial agent to a module of the washer system at the dosing rate provided by the one or more parameters.

6. The method of claim 1, wherein the tracking data further indicates at least one of a group of data items consisting of: (i) a number of times that the textile has been washed in the washer system, (ii) an amount of the antimicrobial agent that has been applied to the textile in prior treatments, (iii) a duration of one or more prior washing cycles, (iv) a duration of one or more treatment cycles, and (v) a type of textile.

7. The method of claim 6, wherein determining the one or more parameters further comprises:
   determining product data corresponding to the identification tag, wherein the product data indicates at least one of the group of data items consisting of: (i) a type of textile, (ii) a material of the textile, and (iii) a manufacture date of the textile; and
   processing the product data and the tracking data to determine the one or more parameters.

8. The method of claim 1, wherein the identification tag is a radio frequency identification (RFID) tag, and
   wherein detecting the identification tag comprises interrogating the identification tag using a RFID reader device.

9. The method of claim 8, wherein the RFID reader device is located in an intake of the washer system.

10. The method of claim 1, wherein the identification tag comprises a barcode, and
    wherein detecting the identification tag comprises scanning the barcode using a barcode scanner.

11. The method of claim 1, wherein detecting the identification tag comprises reading the identification tag using one or more reader devices located in the washer system.

12. The method of claim 11, wherein the one or more reader devices comprise a first reader device in an intake of the washer system, wherein the first reader device is configured to determine that the textile entered the washer system.

13. The method of claim 12, wherein the one or more reader devices further comprise at least one second reader device located between the intake and an discharge of the washer system, wherein the at least one second reader device is configured to track the textile as it moves through the washer system from the intake to the discharge.

14. The method of claim 12, wherein the one or more reader devices further comprise a second reader device located between a main wash zone of the washer system and a rinse zone of the washer system.

15. The method of claim 14, wherein the one or more reader devices further comprise a third reader device located between the rinse zone and a neutralization zone of the washer system.

16. The method of claim 12, further comprising detecting the identification tag using a second reader device located in a treatment zone of the washer system.

17. The method of claim 1, wherein detecting the identification tag comprises:
    detecting the identification tag at a first time when the textile enters a treatment zone of the washer system;
    detecting the identification tag at a second time when the textile exits the treatment zone; and
    determining tracking data for the textile based on the first time, the second time, and the one more parameters used to treat the textile between the first time and the second time.

18. The method of claim 1, further comprising:
    storing, in a data storage unit, tracking data relating to the one or more parameters used to treat the textile.

19. A method, comprising:
    detecting an identification tag coupled to a textile at a first location in a system, wherein the identification tag uniquely identifies the textile;
    responsive to detecting the identification tag at the first location, determining tracking data corresponding to the identification tag, wherein the tracking data includes medical-related information, wherein medical-related information is a medical record associated with at least one user associated with the textile, and wherein the medical record is used to determine information relating to at least one of: (i) one or more medical procedures performed on the user; or (ii) one or more health conditions of the user for a time period during which the user used the textile;
    after detecting the identification tag at the first location, detecting the textile at a second location in the system;
    responsive to detecting the identification tag at the second location, updating the tracking data associated with the textile; and
    treating, based on the tracking data, one or more items in the system with an antimicrobial agent.

20. A washing system for treating a textile with an antimicrobial agent, the washing system comprising:
one or more processors; and
a tangible, non-transitory, computer-readable media storing instructions that, when executed by the one or more processors, cause the washing system to perform functions comprising:
  detecting an identification tag, wherein the identification tag uniquely identifies a textile;
  determining, based on the detected identification tag, one or more parameters for treating the textile with an antimicrobial agent, wherein the antimicrobial agent comprises a metallic ion, and wherein determining the one or more parameters comprises:
    determining tracking data corresponding to the identification tag, wherein the tracking data includes medical-related information, wherein medical-related information is a medical record associated with at least one user associated with the textile, and wherein the medical record is used to determine information relating to at least one of: (i) one or more medical procedures performed on the user; or (ii) one or more health conditions of the user for a time period during which the user used the textile; and
    processing the tracking data to determine the one or more parameters; and
  treating the textile with the antimicrobial agent based on the one or more parameters.

* * * * *